US010227296B2

(12) United States Patent
Söderman et al.

(10) Patent No.: US 10,227,296 B2
(45) Date of Patent: Mar. 12, 2019

(54) BIS(SULFONAMIDE) DERIVATIVES AND THEIR USE AS MPGES INHIBITORS

(71) Applicant: Acturum Real Estate AB, Solna (SE)

(72) Inventors: Peter Söderman, Stockholm (SE);
Mats A. Svensson, Portland, OR (US);
Annika Kers, Stockholm (SE); Liselott Öhberg, Järfälla (SE); Katharina Högdin, Knivsta (SE); Andreas Hettman, Trosa (SE); Jesper Hallberg, Stockholm (SE); Maria Ek, Solna (SE);
Johan Bylund, Therwil (CH); Johan Nord, Västerås (SE)

(73) Assignee: Arcturum Real Estate AB, Solna (SE)

( * ) Notice: Subject to any disclaimer, the term of this patent is extended or adjusted under 35 U.S.C. 154(b) by 0 days.

(21) Appl. No.: 15/529,701

(22) PCT Filed: Nov. 24, 2015

(86) PCT No.: PCT/SE2015/051261
§ 371 (c)(1),
(2) Date: May 25, 2017

(87) PCT Pub. No.: WO2016/085391
PCT Pub. Date: Jun. 2, 2016

(65) Prior Publication Data
US 2018/0002278 A1    Jan. 4, 2018

(30) Foreign Application Priority Data
Nov. 27, 2014  (SE) ...................................... 1451434

(51) Int. Cl.
| A61K 31/18 | (2006.01) |
| C07C 311/44 | (2006.01) |
| A61K 45/06 | (2006.01) |
| C07C 311/39 | (2006.01) |
| C07D 209/08 | (2006.01) |
| C07D 209/34 | (2006.01) |
| A61K 31/277 | (2006.01) |
| A61K 31/404 | (2006.01) |
| A61P 29/00 | (2006.01) |
| A61P 35/00 | (2006.01) |

(52) U.S. Cl.
CPC ............ *C07C 311/44* (2013.01); *A61K 31/18* (2013.01); *A61K 31/277* (2013.01); *A61K 31/404* (2013.01); *A61K 45/06* (2013.01); *A61P 29/00* (2018.01); *A61P 35/00* (2018.01); *C07C 311/39* (2013.01); *C07D 209/08* (2013.01); *C07D 209/34* (2013.01)

(58) Field of Classification Search
None
See application file for complete search history.

(56) References Cited

U.S. PATENT DOCUMENTS

| 2009/0163586 A1 | 6/2009 | Bylund et al. |
| 2010/0292279 A1 | 11/2010 | Bylund et al. |

FOREIGN PATENT DOCUMENTS

| WO | WO 2007/042817 | 4/2007 |
| WO | WO 2008/129276 | 10/2008 |
| WO | WO 2008/129288 | 10/2008 |
| WO | WO 2009/064250 | 5/2009 |
| WO | WO 2009/064251 | 5/2009 |
| WO | WO 2009/082347 | 7/2009 |
| WO | WO 2010/132016 | 11/2010 |

OTHER PUBLICATIONS

Samuelsson, Bengt. Pharmacol Rev 59 (2007) 207-224.*
Psarra, Anastasia. Expert Opinion on Therapeutic Patents (2017) 27(9) 1047-1059.*
Koeberle. Andreas. J. Med. Chem. (2016) 59 5970-5986.*
WebMD. Can you prevent Alzheimer's disease? (2018) Web < https://www.webmd.com/alzheimers/guide/understanding-alzheimers-disease-prevention#1>.*
MedicineNet.com (2004) Web <http://www.medterms.com>.*
WebMD. Sleep Apnea. (2018) Web < https://www.webmd.conn/sleep-disorders/sleep-apnea/sleep-apnea>.*
NIH. National Heart, Lung and Blood Institute. Aneurysm. (2018) Web < https://www.nhlbi.nih.gov/health-topics/aneurysm>.*
Beales et al., "Microsomal Prostaglandin E Synthas-1 inhibition blocks proliferation and enhances apoptosis in oesophageal adenocarcinoma cells without affecting endothelial prostacyclin production", Int. J. Cancer, 126, pp. 2247-2255, 2010.
Chaudhry et al., "Elevated Microsomal Prostaglandin-E Synthase-1 in Alzheimer's Disease", The Journal of the Alzheimer's Association, vol. 4, Issue 1, pp. 3-13, Jan. 2008.
Hernandez et al., "Overexpression of COX-2, Prostaglandin E Synthase-1 and Prostaglandin E Receptors in blood Mononuclear cells and plaque of patients with carotid atherosclerosis: Regulation by nuclear factor—kB", Atherosclerosis 187, pp. 139-149, 2006.
Hofstetter et al., "The Induced Prostaglandin E2 Pathway is a Key regulator of the Respiratory Response to Infection and Hypoxia in Neonates", PNAS, pp. 9894-9899, vol. 104, No. 23, Jun. 2007.

(Continued)

*Primary Examiner* — Deepak R Rao
*Assistant Examiner* — Laura M Daniel
(74) *Attorney, Agent, or Firm* — Baker & Hostetler LLP

(57) ABSTRACT

The present invention relates to bis(sulfonamide) compounds and pharmaceutically acceptable salts thereof. The present invention also relates to pharmaceutical compositions comprising these compounds and to their use as a medicament for the treatment and/or prevention of a disease, disorder or condition in which modulation of microsomal prostaglandin E synthase-1 activity is beneficial, such as pain, inflammation and cancer.

25 Claims, No Drawings

(56) References Cited

OTHER PUBLICATIONS

Isono et al., "Microsomal Prostaglandin E Synthase-1 Enhances Bone Cancer Growth and Bone Cancer-Related pain Behaviors in Mice", Life Sciences, 88, pp. 693-700, 2011.
Jakobsson et al., "Identification of Human Prostaglandin E Synthase: A Microsomal, Glutathione-dependent, Inducible enzyme, Constituting a Potential Novel Drug Target", Proc. Natl. Acad. Sci., vol. 96, pp. 7220-7225, Jun. 1999.
Jarowicki et al., Protecting Groups, J. Chem. Soc., Perkin Trans., 1, pp. 2109-2135, 2001.
Kamata et al., "mPGES-1-Expressing bone Marrow-derived cells enhance tumor growth and Angiogenesis in Mice", Biomedicine & Pharmacotherapy, 64, pp. 409-416, 2010.
Kojima et al., "Prostaglandin E Synthase in the Pathophysiology of Arthritis", Fundamental & Clinical Pharmacology, 19, pp. 255-261, 2005.
Kojima et al., Defective Generation of Humoral Immune Response Is Associate with a Reduced Incidence and Severity of Collagen-Induced Arthritis in Microsomal Prostaglandin E Synthase-1 Null Mice, J Immunol, 180(12), pp. 8361-8368, Jun. 2008.
Korotkova et al., "Effects of Immunosuppressive Treatment on Microsomal Prostaglandin E Synthase 1 and Cyclooxygenases Expression in Muscle Tissue of Patients with Polymyositis or Dermatomyositis", Ann Rheum Dis, 67(11), pp. 1596-1602, 2008.
Lu et al., "Microsomal Prostaglandin E Synthase-1 Promotes Hepatocarcinogenesis through Activation of a Novel EGR1 / β-Catenin Signaling Axis", Nature, 31, pp. 842-857, 2012.
Menter et al., "Prostaglandins in Cancer Cell Adhesion, Migration, and Invasion", Hindawi Publishing Corporation International Journal of Cell Biology, vol. 2012, 21 pages, 2012.
Nakanishi et al., "Genetic Deletion of mPGES-1 Suppresses Intestinal Tumorigenesis", Cancer Research, 68(9), May 2008.
Nakanishi et al., mPGES-1 as a Target for Cancer Suppression: A Compreshensive invited review "Phospholipase $A_2$ and Lipid Mediators", Biochimie, 92(6), pp. 660-664, Jun. 2010.
Patrignani et al., "Biochemical and Pharmacological Characterization of the Cyclooxygenase Activity of Human Blood Prostaglandin Endoperoxide Synthases", The Journal of Pharmacology and Experimental Therapeutics, vol. 271, No. 3, pp. 1705-1712, Aug. 1994.
Schroder et al., "15-deoxy-$^{12,14}$ prostaglandin $J^2$ Inhibits the Expression of Microsomal Prostaglandin E Synthase Type 2 in Colon Cancer Cells", Journal of Lipid Research, vol. 47, 2006.
Wang et al., "Clinical Implications of Microsomal Prostaglandin E Synthase-1 Overexpression in Human Non-Small-Cell Lung Cancer" Annals of Surgical Oncology, 13(9), pp. 1224-1234, Sep. 2006.
Wang et al., "Deletion of Microsomal Prostaglandin E Synthase-1 Augments Prostacyclin and Retards Atherogenesis" PNAS, vol. 103, No. 39, pp. 14507-14512, Sep. 2006.
Wang et al., "Microsomal Prostaglandin E Synthase-1 Deletion Suppresses Oxidative Stress and Angiotensin II-Induced Abdominal Aortic Aneurysm Formation" Vascular Medicine, 117(10), pp. 1302-1309, 2008.
Wang et al., Microsomal Prostaglandin E2 Synthase-1 Modulates the Response to Vascular Injury, Circulation, 123(6), pp. 631-639, 2011.
Xu et al., "MF63 [2-(6-Chloro-1H-Phenanthro[9,10-d]imidazole-2-yl)-isophthalonitrile], a selective Microsomal Prostaglandin E Synthase-1 Inhibitor, Relieves Pyresis and Pain in Preclinical Models of Inflammation", Journal of Pharmacology and Experimental Therapeutics, vol. 326, No. 3, May 2008.

* cited by examiner

BIS(SULFONAMIDE) DERIVATIVES AND THEIR USE AS MPGES INHIBITORS

CROSS-REFERENCE TO RELATED APPLICATIONS

This application is the National Stage of International Application No. PCT/EP2015/051261, filed Nov. 24, 2015, which claims the benefit of SE application number 1451434-3, filed Nov. 27, 2014, the disclosures of which are incorporated herein by reference in their entireties.

FIELD OF THE INVENTION

The present invention relates to bis(sulfonamide) compounds and pharmaceutically acceptable salts thereof. The present invention also relates to pharmaceutical compositions comprising these compounds, and to their use as medicaments for the treatment and/or prevention of a disease, disorder or condition in which modulation of microsomal prostaglandin E synthase-1 activity is beneficial, such as pain, inflammation and cancer.

BACKGROUND

Modulation of prostaglandin metabolism is at the centre of current anti-inflammatory therapies. NSAIDs and COX-2 inhibitors block the activity of cyclooxygenases and their ability to convert arachidonic acid into prostaglandin H2 (PGH2). PGH2 can be subsequently metabolized by terminal prostaglandin synthases to the corresponding biologically active PGs, namely, PGI2, thromboxane (Tx) A2, PGD2, PGF2a and PGE2. A combination of pharmacological, genetic and neutralizing antibody approaches demonstrates the importance of PGE2 in inflammation. The conversion of PGH2 to PGE2 by prostaglandin E synthases (PGES) may therefore represent a pivotal step in the propagation of inflammatory stimuli.

Microsomal prostaglandin E synthase-1 (mPGES-1) is an inducible PGES after exposure to pro-inflammatory stimuli. mPGES-1 is induced in the periphery and in the CNS by inflammation and represents therefore a target for acute and chronic inflammatory disorders.

PGE2 is a major prostanoid driving inflammatory processes. The prostanoid is produced from arachidonic acid liberated by Phospholipases (PLAs). Arachidonic acid is transformed by the action of Prostaglandin H Synthase (PGH Synthase, cyclooxygenase) into PGH2, which is a substrate for mPGES-1, which is the terminal enzyme transforming PGH2 to the pro-inflammatory PGE2.

NSAIDs reduce PGE2 by inhibiting cyclooxygenase, but at the same time reducing other prostanoids, giving side effects such as ulcerations in the GI tract. mPGES-1 inhibition gives a similar effect on PGE2 production without affecting the formation of other prostanoids, and hence a more favourable profile.

By blocking the formation of PGE2 in animal models of inflammatory pain a reduced inflammation, pain and fever response has been demonstrated (see e.g. Kojima et. al, *The Journal of Immunology* 2008, 180(12): 8361-8368; Xu et al., *The Journal of Pharmacology and Experimental Therapeutics* 2008, 326(3): 754-763).

Osteoarthritis is an inflammation of one or more joints, caused by the loss of cartilage leading to loss of water, while rheumatoid arthritis is considered to be of autoimmune origin. In several models of arthritis, inhibition of mPGES-1 leads to a reduced inflammation and/or pain (Kojima et al., *Fundamental & Clinical Pharmacology* 2005, 19(3): 255-261).

In abdominal aortic aneurism, inflammation leads to connective tissue degradation and smooth muscle apoptosis ultimately leading to aortic dilation and rupture. In animals lacking mPGES-1 a slower disease progression and disease severity has been demonstrated (see e.g. Wang et al., *Circulation* 2008, 117(10): 1302-1309).

Several lines of evidence indicate that PGE2 is involved in malignant growth. PGE2 facilitates tumor progression of many different types of cancers, by stimulation of cellular proliferation and angiogenesis and by modulation of immunosuppression (see e.g. Menter et al., *International Journal of Cell Biology* 2012; Nakanishi et al., *Biochimie* 2010, 92(6): 660-664; Kamata et al., *Biomedicine & Pharmacotherapy* 2010, 64(6): 409-416; Beales et al., *Int. J. Cancer* 2010, 126(9): 2247-2255). In support of a role for PGE2 in carcinogenesis, genetic deletion of mPGES-1 in mice suppresses the intestinal tumourogenesis (Nakanishi et al., *Cancer Research* 2008, 68(9): 3251-3259), hepatocarcinogenesis (Lu et al., *Oncogene* 2012, 31(7): 842-857) and bone cancer (Isono et al., *Life Sciences* 2011, 88(15-16): 693-700). In man, mPGES-1 is also upregulated in cancers such as colorectal cancer (see e.g. Schröder et al., *Journal of Lipid Research* 2006, 47(5): 1071-80) and non-small-cell lung cancer (NSCLS) (Wang et al., *Annals of Surgical Oncology* 2006, 13(9): 1224-1234).

Myositis is chronic muscle disorder characterized by muscle weakness and fatigue.

Proinflammatory cytokines and prostanoids have been implicated in the development of myositis. In skeletal muscle tissue from patients suffering from myositis, an increase in cyclooxygenases and mPGES-1 has been demonstrated, implicating mPGES-1 as a target for treating this condition (see e.g. Korotkova et al., *Annals of the Rheumatic Diseases* 2008, 67(11): 1596-1602).

In atherosclerosis, inflammation of the vasculature leads to atheroma formation that eventually may progress into infarction. In patients with carotid atherosclerosis, an increase in mPGES-1 in plaque regions has been found (Gómez-Hernández et al., *Atherosclerosis* 2006, 187(1): 139-149). In an animal model of atherosclerosis, mice lacking the mPGES-1 receptor were found to show a retarded atherogenesis and a concomitant reduction in macrophage-derived foam cells together with an increase in vascular smooth muscle cells (see e.g. Wang et al., *Proceedings of National Academy of Sciences* 2006, 103(39): 14507-14512) and reduced neointimal hyperplasia (Wang et al. *Circulation* 2011, 123(6): 631-639).

PGE-2, produced via mPGES-1, exerts a control of apnea frequency and mPGES-1 KO mice show reduced sensitivity to IL-1 induced anoxia (Hofstetter et al., *Proceedings of National Academy of Sciences* 2007, 104(23), 9894-9899).

Inflammation is part of the Alzheimer pathology, and mPGES-1 levels are higher in neuronal tissue from AD patients (Chaudhry et al., *Alzheimer's & Dementia* 2008, 4(1): 6-13).

Bis(sulfonamide) compounds which are useful for the treatment of pain and inflammatory diseases have been suggested in WO2007/042817, WO2008/129276, WO2008/129288, WO2009/064250, WO2009/064251, WO2009/082347 and WO2010/132016.

There is still a need for compounds that have an improved potency and improved selectivity to PGE2. There is a need for compounds having reduced side effect, such as gastrointestinal and renal toxicity.

SUMMARY OF THE INVENTION

The present invention is directed to a compound of formula (I), or a pharmaceutically acceptable salt thereof

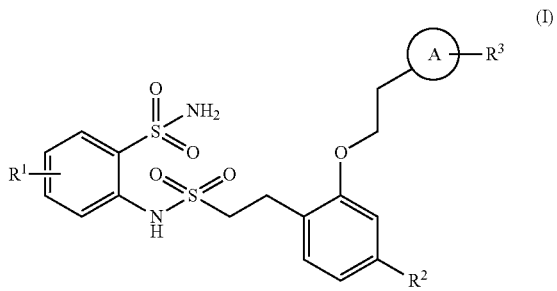

wherein:
A is phenyl or a saturated or unsaturated 9 or 10 membered-ring optionally comprising one or two heteroatoms selected from 0 and N;
$R^1$ is H, halogen or —$CH_2OH$;
$R^2$ is H, halogen, $C_{1-4}$-alkyl, fluoro-$C_{1-4}$-alkyl or —C≡C—$R^4$;
$R^3$ is H, halogen, $C_{1-4}$-alkyl, $C_{1-4}$-alkoxy, cyano or oxo; and
$R^4$ is $C_{1-4}$-alkyl, $C_{3-7}$-cycloalkyl or phenyl, wherein phenyl is optionally substituted with one or more substituents independently selected from $C_{1-4}$-alkyl, halogen, $C_{1-4}$-alkoxy and cyano.

One embodiment relates to the compound of formula (I), wherein A is phenyl and $R^1$ is H. In another embodiment A is indolyl or dihydroindolyl and $R^1$ is H.

Compounds of formula (I), whereby $R^1$ is H have good binding properties.

Another embodiment relates to the compound of formula (I), wherein A is phenyl and $R^2$ is chlorine. In another embodiment A is indolyl or dihydroindolyl and $R^2$ is chlorine.

Compounds of formula (I), whereby $R^2$ is chlorine have good binding properties.

A further embodiment relates to the compound of formula (I), wherein A is phenyl and $R^3$ is H, $C_{1-2}$-alkoxy or cyano. $R^3$ may be substituted at the para- meta- or ortho-position. In another embodiment A is indolyl or dihydroindolyl and $R^3$ is H, $C_{1-2}$-alkyl or oxo.

The novel bis(sulfonamide) compounds are selective inhibitors of the microsomal prostaglandin E synthase-1 enzyme. The compounds are believed to have an improved potency and selectivity by selectively inhibiting the pro-inflammatory PGE2. It is believed that the compounds of the invention would have a reduced potential for side effects associated with the inhibition of other prostaglandins compared to conventional non-steroidal anti-inflammatory drugs. The compounds of the invention are believed to have a reduced gastrointestinal and renal toxicity.

One embodiment relates to the compound of formula (I), wherein
A is phenyl, indolyl or dihydroindolyl;
$R^1$ is H or —$CH_2OH$;
$R^2$ is H, bromine, chlorine, fluorine, $C_{1-4}$-alkyl, fluoro-$C_{1-4}$-alkyl or —C≡C—$R^4$;
$R^3$ is H, bromine, chlorine, fluorine, $C_{1-4}$-alkyl, $C_{1-4}$-alkoxy, cyano or oxo; and
$R^4$ is $C_{1-4}$-alkyl, $C_{3-7}$-cycloalkyl or phenyl, wherein phenyl is optionally substituted with $C_{1-4}$-alkyl.

A further embodiment relates to the compound of formula (I), wherein
A is phenyl, indolyl or dihydroindolyl;
$R^1$ is H;
$R^2$ is chlorine; and
$R^3$ is H, $C_{1-2}$-alkyl, $C_{1-2}$-alkoxy, cyano or oxo.

Another embodiment relates to the compound of formula (I), wherein
A is phenyl;
$R^1$ is H or —$CH_2OH$;
$R^2$ is H, chlorine, $C_{1-4}$-alkyl or fluoro-$C_{1-4}$-alkyl; and
$R^3$ is H, $C_{1-2}$-alkyl, $C_{1-2}$-alkoxy, cyano or oxo.

One embodiment relates to the compound of formula (I), wherein
A is phenyl;
$R^1$ is H or —$CH_2OH$;
$R^2$ is chlorine; and
$R^3$ is H, methoxy or cyano.

The selectivity and/or potency can be improved by compounds of formula (I), whereby the substituents on $R^1$ and X, are relatively short.

A further embodiment relates to the compound of formula (I), wherein
A is indolyl or dihydroindolyl;
$R^1$ is H;
$R^2$ is H, chlorine, $C_{1-4}$-alkyl or fluoro-$C_{1-4}$-alkyl; and
$R^3$ is H, $C_{1-2}$-alkyl, $C_{1-2}$-alkoxy, cyano or oxo.

A further embodiment relates to the compound of formula (I), wherein
A is indolyl or dihydroindolyl;
$R^1$ is H;
$R^2$ is chlorine; and
$R^3$ is H, methyl, or oxo.

The selectivity and/or potency can be improved by compounds of formula (I), whereby the substituents on $R^1$ and $R^2$, are relatively short.

The invention also relates to any one of a compound, or a pharmaceutically acceptable salt thereof, selected from
2-(2-(4-chloro-2-phenethoxyphenyl)ethylsulfonamido)benzenesulfonamide,
2-(2-(4-chloro-2-(2-methoxyphenethoxy)phenyl)ethylsulfonamido)benzenesulfonamide,
2-(2-(4-chloro-2-(3-methoxyphenethoxy)phenyl)ethylsulfonamido)benzenesulfonamide,
2-(2-(4-chloro-2-(4-methoxyphenethoxy)phenyl)ethylsulfonamido)benzenesulfonamide,
2-(2-(4-chloro-2-(2-cyanophenethoxy)phenyl)ethylsulfonamido)benzenesulfonamide,
2-(2-(4-chloro-2-(3-cyanophenethoxy)phenyl)ethylsulfonamido)benzenesulfonamide,
2-(2-(4-chloro-2-(4-cyanophenethoxy)phenyl)ethylsulfonamido)benzenesulfonamide,
2-(2-(4-chloro-2-(2-(1-methyl-1H-indol-4-yl)ethoxy)phenyl)ethylsulfonamido)benzenesulfonamide,
2-(2-(4-chloro-2-(2-(2-oxoindolin-4-yl)ethoxy)phenyl)ethylsulfonamido)benzenesulfonamide, and
2-(2-(4-chloro-2-phenethoxyphenyl)ethylsulfonamido)-5-(hydroxymethyl)benzenesulfonamide.

These compounds fall within the scope of compounds of formula (I). It is to be understood that this list of compounds is included in the wording "compound of formula (I), or a pharmaceutically acceptable salt thereof", as used in embodiments related to uses, pharmaceutical compositions or processes, unless specified otherwise.

The invention also relates to the compound of formula (I), or a pharmaceutically acceptable salt thereof, as defined above, for use in therapy. In an embodiment, the invention relates to a compound of formula (I), or a pharmaceutically acceptable salt thereof, for use in the treatment or prevention of a disease, disorder or condition in which modulation of microsomal prostaglandin E synthase-1 activity is beneficial, such as pain, cancer, inflammation, apnea, sudden infant death (SID), atherosclerosis, aneurysm, hyperthermia, myositis, Alzheimer's disease, arthritis, osteoarthritis, rheumatoid arthritis, stroke or dementia. One embodiment relates to a use of the compound of formula (I), or a pharmaceutically acceptable salt thereof, as defined above, in therapy.

Another embodiment relates to the compound of formula (I), or a pharmaceutically acceptable salt thereof, as defined above, for use in prevention and/or treatment of pain.

A further embodiment relates to the compound of formula (I), or a pharmaceutically acceptable salt thereof, as defined above, for use in prevention and/or treatment of acute or chronic pain, nociceptive pain or neuropathic pain. Another embodiment relates to the compound of formula (I), or a pharmaceutically acceptable salt thereof, as defined above, for use in prevention and/or treatment of nociceptive pain. In one embodiment, the invention relates to a compound of formula (I), or a pharmaceutically acceptable salt thereof, for use in the treatment or prevention of inflammatory pain, headache and musculoskeletal pain.

One embodiment relates to the compound of formula (I), or a pharmaceutically acceptable salt thereof, as defined above, for use in prevention and/or treatment of cancer. Another embodiment relates to the compound of formula (I), or a pharmaceutically acceptable salt thereof, as defined above, for use in prevention and/or treatment of bone cancer, colorectal cancer, non-small-cell lung cancer or benign or malignant neoplasias.

Another embodiment relates to a use of the compound of formula (I), or a pharmaceutically acceptable salt thereof, as defined above, for use in the prevention and/or treatment of inflammation.

A further embodiment relates to the compound of formula (I), or a pharmaceutically acceptable salt thereof, as defined above, for use in the prevention and/or treatment of apnea, sudden infant death (SID), atherosclerosis, aneurysm, hyperthermia, myositis, Alzheimer's disease or arthritis.

Another embodiment relates to the compound of formula (I), or a pharmaceutically acceptable salt thereof, as defined above, for use in prevention and/or treatment of osteoarthritis or rheumatoid arthritis.

One embodiment relates to the compound of formula (I), or a pharmaceutically acceptable salt thereof, as defined above, for use in prevention and/or treatment of stroke or dementia.

The invention relates to a method of treating, preventing or reducing the risk of, a disease, disorder or condition in which modulation of microsomal prostaglandin E synthase-1 activity is beneficial, which comprises administering to a mammal, such as a human, in need thereof, a therapeutically effective amount of a compound of formula (I) as defined above or a pharmaceutically acceptable salt thereof.

The invention further relates to a pharmaceutical composition comprising the compound of formula (I), as defined above, or a pharmaceutically acceptable salt thereof, in the association with a pharmaceutically acceptable adjuvant, dilutent or carrier.

The invention also relates to a process for the preparation of a pharmaceutical composition, as defined above, which comprises mixing a compound of formula (I), as defined above, or a pharmaceutically acceptable salt thereof, with a pharmaceutically acceptable adjuvant, diluent or carrier.

One embodiment relates to a use of the pharmaceutical composition, as defined above, in therapy, or for the prevention and/or treatment of a disease, disorder or condition in which modulation of microsomal prostaglandin E synthase-1 activity. Examples of such disease, disorder or condition are mentioned above.

The invention also relates to the use of a compound of formula (I), or a pharmaceutically acceptable salt thereof, as defined above, in the manufacture of a medicament for the treatment or prevention of a disease, disorder or condition in which modulation of microsomal prostaglandin E synthase-1 activity is beneficial. Examples of such disease, disorder or condition are mentioned above.

The treatment of microsomal prostaglandin E synthase-1 activity related pathology defined herein may be applied as a sole therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents, or atypical antipsychotic agents. Cognitive enhancing agents, memory enhancing agents and acetyl choline esterase inhibitors include onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX).

Such conjoint treatment may be achieved by way of the simultaneous, sequential or separate dosing of the individual components of the treatment. Such combination products employ the compounds, or pharmaceutically acceptable salts thereof, of the invention.

In one embodiment, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) a pharmaceutically acceptable excipient, carrier or diluent.

In another embodiment, the invention relates to a pharmaceutical composition comprising (i) a compound of formula (I), or a pharmaceutically acceptable salt thereof, (ii) at least one agent selected from the group consisting of acetyl cholinesterase inhibitors, anti-inflammatory agents, cognitive enhancing agents, memory enhancing agents, and atypical antipsychotic agents, and (iii) a pharmaceutically acceptable excipient, carrier or diluent.

In another embodiment, the invention relates to a pharmaceutical composition comprising (i) a compound of formula (I), or a pharmaceutically acceptable salt thereof, (ii) at least one agent selected from the group consisting of onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX), and (iii) a pharmaceutically acceptable excipient, carrier or diluent.

Additional conventional chemotherapy or therapy may include one or more of the following categories of agents:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine and venlafaxine.
(ii) atypical antipsychotics such as quetiapine.
(iii) antipsychotics such as amisulpride, aripiprazole, asenapine, benziosxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine and ziprasidone.
(iv) anxiolytics such as alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam and zolazepam.
(v) anticonvulsants such as carbamazepine, clonazepam, ethosuximide, felbamate, fosphenytoin, gabapentin, lacosamide, lamotrigine, levetiracetam, oxcarbazepine, phenobarbital, phenytoin, pregabaline, rufinamide, topiramate, valproate, vigabatrine and zonisamide.
(vi) Alzheimer's therapies such as donepezil, memantine, rivastigmine, galantamine and tacrine.
(vii) Parkinson's therapies such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase.
(viii) migraine therapies such as almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan and zomitriptan.
(ix) stroke therapies such as abciximab, activase, NXY-059, citicoline, crobenetine, desmoteplase, repinotan, clopidogrel, eptifibatide, minocycline and traxoprodil.
(x) urinary incontinence therapies such as darafenacin, falvoxate, oxybutynin, propiverine, robalzotan, solifenacin and tolterodine.
(xi) neuropathic pain therapies including for example lidocain and capsaicin, and anticonvulsants such as gabapentin and pregabalin, and antidepressants such as duloxetine, venlafaxine, amitriptyline and klomipramine.
(xii) nociceptive pain therapies such as paracetamol; NSAIDS such as diclofenac, loxoprofen, naproxen, ketoprofen, ibuprofen, nabumeton, meloxicam and piroxicam; coxibs such as celecoxib, etoricoxib, lumiracoxib, rofecoxib, valdecoxib and parecoxib; and opioids such as morphine, oxycodone, buprenorfin and tramadol.
(xiii) insomnia therapies such as agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon and zolpidem.
(xiv) mood stabilizers such as carbamazepine, divalproex, gabapentin, lamotrigine, lithium, olanzapine, quetiapine, valproate, valproic acid and verapamil.

Such combination products employ the compounds of this invention within the dosage range described herein and the other pharmaceutically active compound or compounds within approved dosage ranges and/or the dosage described in the publication reference.

DETAILED DESCRIPTION OF THE INVENTION

The definitions set forth in this application are intended to clarify terms used throughout this application. The term "herein" means the entire application.

As used herein, the term "$C_{1-4}$-alkyl", used alone or as a suffix or prefix, is intended to include both branched and straight chain saturated aliphatic hydrocarbon groups having from 1 to 4 carbon atoms. Examples of $C_{1-4}$-alkyl include methyl, ethyl, n-propyl, i-propyl, n-butyl, i-butyl, sec-butyl and tert-butyl.

As used herein, the term "$C_{1-4}$-alkoxy", used alone or as a suffix och prefix, refers to a $C_{1-4}$-alkyl radical, which is attached to the remainder of the molecule through an oxygen atom. Examples of $C_{1-4}$-alkoxy include methoxy, ethoxy, n-propoxy, i-propoxy, n-butoxy, i-butoxy, sec-butoxy and tert-butoxy.

As used herein, the term "fluoro-$C_{1-4}$-alkyl", used alone or as a suffix or prefix, is intended to include both branched and straight chain saturated aliphatic hydrocarbon groups, having at least one fluoro substituent and having from 1 to 4 carbon atoms. Examples of fluoro-$C_{1-4}$-alkyl include, but are not limited to, fluoromethyl, difluoromethyl, trifluoromethyl, 1-fluoroethyl, difluoroethyl, trifluoroethyl, fluoropropyl, difluoropropyl, trifluoropropyl, fluorobutyl, difluorobutyl and trifluorobutyl.

As used herein, the term "$C_{3-7}$-cycloalkyl", used alone or as suffix or prefix, denotes a cyclic saturated alkyl group having a ring size from 3 to 7 carbon atoms and includes cyclopropyl, cyclobutyl, cyclopentyl, cyclohexyl and cycloheptyl.

As used herein, the term "halogen" or "halo", used alone or as suffix or prefix, is intended to include bromine, chlorine, fluorine or iodine.

As used herein, the term "optional" or "optionally" means that the subsequently described event or circumstance may but need not occur, and that the description includes instances where the event or circumstance occurs and instances where it does not.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "protecting group" means temporary substituents protecting a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been extensively reviewed (see, e.g.

Jarowicki, K.; Kocienski, P. Perkin Trans. 1, 2001, issue 18, p. 2109). As used herein, "pharmaceutically acceptable salts" refer to forms of the disclosed compounds, wherein the parent compound is modified by making acid or base salts thereof. Examples of pharmaceutically acceptable salts include, but are not limited to, mineral or organic acid salts of basic residues such as amines; alkali or organic salts of acidic residues, such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

A variety of compounds in the present invention may exist in particular geometric or stereoisomeric forms. The present invention takes into account all such compounds, including tautomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. All chiral, diastereomeric and racemic forms are intended, to be included in the scope of the invention, unless the specific stereochemistry or isomeric form is specifically indicated.

As used herein, "tautomer" means other structural isomers that exist in equilibrium resulting from the migration of a hydrogen atom. For example, keto-enol tautomerism occurs where the resulting compound has the properties of both a ketone and an unsaturated alcohol.

As used herein, the phrase "compounds or pharmaceutically acceptable salts" include hydrates and solvates thereof.

Compounds and salts described in this specification may be isotopically-labelled compounds (or "radio-labelled"). In that instance, one or more atoms are replaced by an atom having an atomic mass or mass number different from the atomic mass or mass number typically found in nature (i.e., naturally occurring). Examples of suitable isotopes that may be incorporated include $^2$H (also written as "D" for deuterium), $^3$H (also written as "T" for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is used will depend on the specific application of that radio-labelled derivative. For example, for in vitro receptor labelling and competition assays, compounds that incorporate $^3$H or $^{14}$C are often useful. For radio-imaging applications $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The optimum dosage and frequency of administration will depend on the particular condition being treated and its severity; the age, sex, size and weight, diet, and general physical condition of the particular patient; other medication the patient may be taking; the route of administration; the formulation; and various other factors known to physicians and others skilled in the art.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

Preparation of Compounds

Compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3$^{rd}$ Edition, Wiley-Interscience, New York, 1999.

General Methods

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

Microwave heating was performed in a Biotage Creator, Initiator or Smith Synthesizer Single-mode microwave cavity producing continuous irradiation at 2450 MHz. It is understood that microwaves (MW) can be used for the heating of reaction mixtures.

Thin layer chromatography (TLC) was performed on Merck TLC-plates (Silica gel 60 $F_{254}$) and spots were UV visualized. Straight phase flash column chromatography ("flash chromatography") was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.

NMR

NMR spectra were recorded on a 400-600 MHz NMR spectrometer fitted with a probe of suitable configuration. Spectra were recorded at room temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS Analyses:

High pressure liquid chromatography (HPLC) was performed on a reversed phase (RP) column. A linear gradient was applied using for example mobile phase A (10 mM $NH_4OAc$ in 5% $CH_3OH$ or 5% $CH_3CN$ (aq.), or 0.1% $NH_3$ (aq.) or 0.1% formic acid (aq.)) and B ($CH_3OH$ or $CH_3CN$). Mass spectrometry (MS) analyses were performed in positive and/or negative ion mode using electrospray ionization (ESI+/−) and/or atmospheric pressure chemical ionization (APCI+/−).

GCFID and GCMS Analyses:

Gas chromatography (GC) was performed on a GC equipped with a mass spectrometer (MS) or a flame ionization detector (FID). The MS ion source was either an electron impact (EI) or a chemical ionization (CI, reactant gas methane). For separation, a capillary column was used for example DB-5MS, (J&W Scientific). A linear temperature gradient was applied.

Preparative Chromatography:

Preparative chromatography was run on a Waters FractionLynx system with an Autosampler combined Automated Fraction Collector (Waters 2767), Gradient Pump (Waters 2525), Column Switch (Waters CFO) and PDA (Waters 2996). Column; XBridge® Prep C8 10 µm OBD™ 19×300 mm, with guard column; XTerra® Prep MS C8 10 µm 19×10 mm Cartridge. A gradient of A (95% 0.1 M $NH_4OAc$ in MilliQ water and 5% MeCN) in B (100% MeCN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min. Preparative chiral chromatography for separation of isomers was run on for example an LaPrep® system using the specified column and mobile phase system.

SFC Analyses:

Supercritical Fluid Chromatography (SFC) was performed on a straight phase column. An isocratic flow was applied using mobile phase A ($CO_2$) and for example mobile phase B (MeOH, EtOH or IPA).

Straight Phase HPLC Analyses:

High pressure liquid chromatography (HPLC) was performed on a straight phase column. A linear gradient or isocratic flow was applied using for example mobile phase A (Heptane) and B (EtOH or IPA).

High-Resolution Mass Spectrometry (HRMS):

For accurate mass measurements, HRMS was performed on a Waters Synapt-G2 mass spectrometer equipped with a LockSpray source and connected to an Acquity UPLC system with a PDA detector and an Acquity UPLC BEH C18 column. The measured mass confirmed the elemental composition within 3 ppm.

Abbreviations

ACN acetonitrile
aq aqueous
Atm atmospheric pressure
Boc t-butoxycarbonyl
Borax di-sodium tetraborate or sodium borate or sodium tetraborate
Cbz benzyloxycarbonyl
CDI 1,1'-carbonyldiimidazole
dba dibenzylideneacetone
DCM dichloromethane
DEA diethylamine
DIBAL-H diisobutylaluminium hydride
DIPEA diisopropylethylamine
DMAP 4-Dimethylaminopyridine
DME 1,2-dimethoxyethane
DMF N,N-dimethyl formamide
DMSO dimethyl sulfoxide
dppf 1,1'-bis(diphenylphosphino)ferrocene
$Et_2O$ diethyl ether
EtOAc ethyl acetate
EtOH ethanol
eq. or equiv. equivalent
h hour(s)
HPLC high performance liquid chromatography
IPA isopropanol
LCMS liquid chromatography mass spectrometry
LiHMDS lithium bis(trimethylsilyl)amide
MeOH methanol
min minute(s)
MS mass spectrometry
MW microwave(s)
$NH_4OAc$ ammonium acetate
NMR nuclear magnetic resonance
ox oxidation
Psi pounds per square inch
quant. quantitative
RCM ring closing metathesis
r.t. room temperature, i.e. between 16 to 25° C. Celcius
sat. saturated
SFC supercritical fluid chromatography
TFA trifluoroacetic acid
THF tetrahydrofuran
TLC thin layer chromatography
TMEDA tetramethylethylenediamine
UPLC ultra performance liquid chromatography
2-Me THF 2-methyl tetrahydrofuran Naming Compounds:

Compounds have been named using CambridgeSoft MedChem ELN v2.2 or ACD/Name, version 10.0, or 10.06, or version 12.01, software from Advanced Chemistry Development, Inc. (ACD/Labs), Toronto ON, Canada, www.acdlabs.com, or Lexichem, version 1.9, software from OpenEye.

General methods

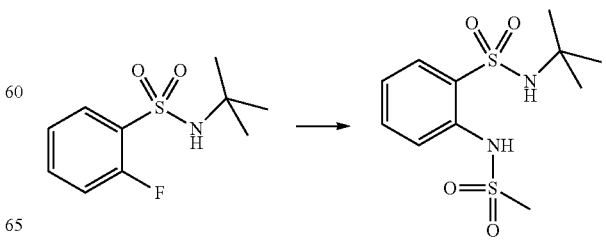

Scheme 1
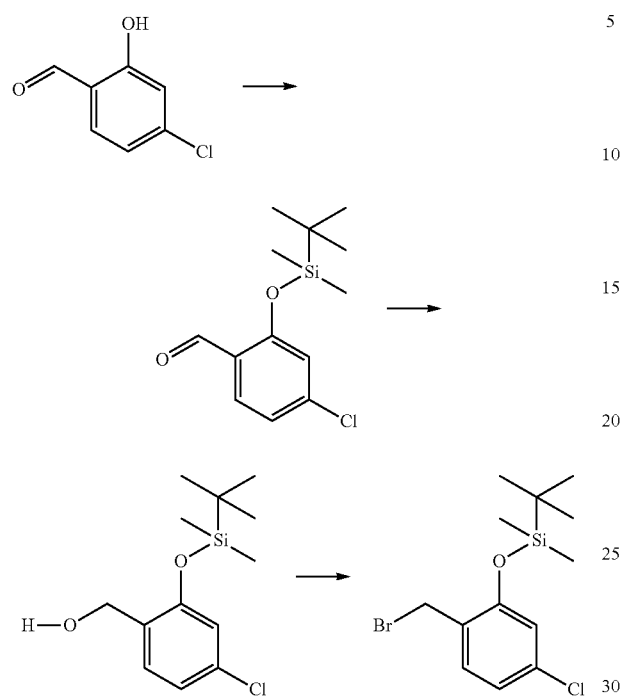
Scheme 2
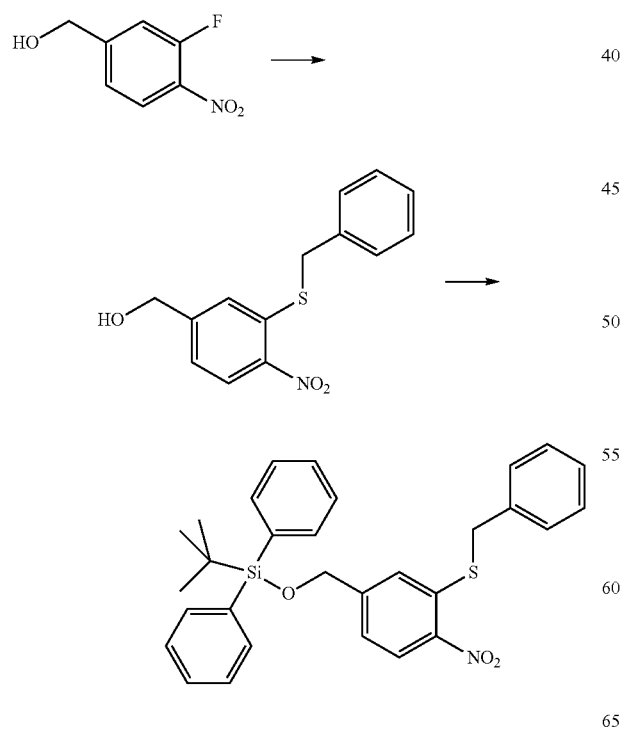
Scheme 3
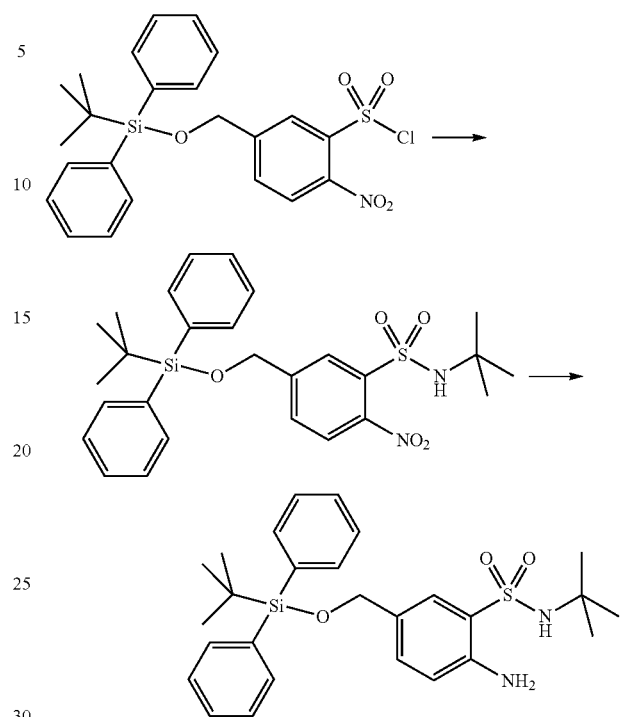
Scheme 4

Scheme 5

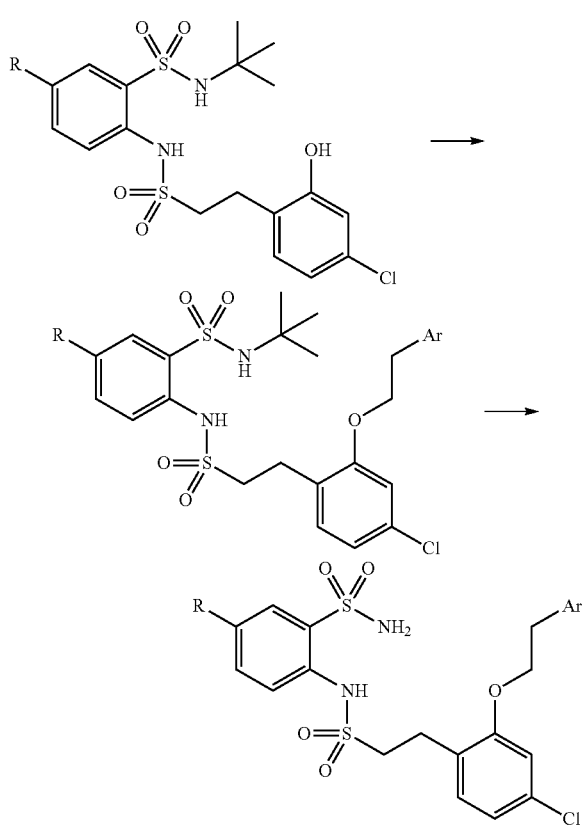

Scheme 6

EXAMPLES

Below follows a number of non-limiting examples of compounds of the invention.

Intermediate 1

N-tert-butyl-2-fluorobenzenesulfonamide

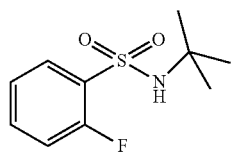

tert-Butylamine (5.0 mL, 47.58 mmol) was added dropwise to a cooled (0° C.) solution of 2-fluorobenzenesulfonyl chloride (2.50 mL, 18.88 mmol) in dichloromethane (15 mL) and the resulting mixture was stirred at 0° C. for 1 h and at room temperature for 1 h. Water and ethyl acetate was added and the aqueous phase was extracted with ethyl acetate. The combined organic phases were washed with water and brine, dried over sodium sulfate and the solvent was evaporated, yielding the title compound (4.37 g, 100%). $^1$H NMR (500 MHz, DMSO-$d_6$) δ ppm 1.11 (s, 9H), 7.34-7.38 (m, 1H), 7.38-7.43 (m, 1H), 7.64-7.70 (m, 1H), 7.77 (br. s., 1H), 7.82 (m, J=7.60, 7.60, 1.70 Hz, 1H); MS (ES$^-$) m/z 230 [M-H]$^-$.

Intermediate 2

N-tert-butyl-2-[(methylsulfonyl)amino]benzenesulfonamide

A mixture of N-tert-butyl-2-fluorobenzenesulfonamide (18.0438 g, 78.01 mmol), Methanesulfonamide (Intermediate 1, 11.2341 g, 118.10 mmol) and potassium carbonate (16.2806 g, 117.80 mmol) in sulfolane (70 mL) was heated at 150° C. over 72 h. Water was added and the resulting solid was removed by filtration. The aqueous phase was neutralized (pH~7.5) with hydrochloric acid (2 M) and extracted with ethyl acetate. The organic phase was washed with water, water/brine (1:1) and brine, dried over magnesium sulfate and the solvent was evaporated. Purification by chromatography on silica using gradient elution 60% EtOAc in heptane., yielded the title compound (17.22 g, 72.0%). $^1$H NMR (500 MHz, DMSO-$d_6$) δ ppm 1.11 (s, 9H) 3.17 (s, 3H) 7.32 (s, 1H) 7.60-7.71 (m, 2H) 7.89 (d, J=7.88 Hz, 1H) 8.01 (s, 1H) 8.72 (s, 1H).

Intermediate 3

4-Chloro-2-{[tert-butyl(dimethyl)silyl]oxy}benzaldehyde

Tert-Butyldimethylchlorosilane (1.426 mL, 7.66 mmol) was added to a solution of 4-chloro-2-hydroxybenzaldehyde (1.0 g, 6.39 mmol) and Imidazole (0.652 g, 9.58 mmol) in DMF (15 mL) at 0° C. The reaction mixture was allowed to reach room temperature and stirred over 72 h. The reaction mixture was concentrated and purification by chromatography on silica using 25% EtOAc in heptane, yielded the title compound (1.1 g, 64%); $^1$H NMR (500 MHz, CHLOROFORM-d) δ ppm 0.26-0.38 (m, 6H) 1.03 (s, 10H) 6.89 (d, 1H) 7.04 (dd, 1H) 7.76 (d, 1H) 10.39 (s, 1H).

Intermediate 4

(2-{[tert-butyl(dimethyl)silyl]oxy}-4-chlorophenyl)methanol

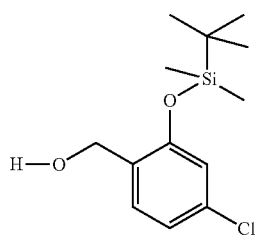 [SMILES: CC(C)(C)[Si](C)(C)Oc1cc(Cl)ccc1CO]

In a 500 mL round bottle was 2-{[tert-butyl(dimethyl)silyl]oxy}-4-chlorobenzaldehyde (26.5 g, 97.85 mmol) dissolved in anhydrous methanol (170 mL) and the solution was cooled to −20° C. with an acetone-dry ice bath. Sodium borohydride (4.44 g, 117.42 mmol) was added in small portions, keeping the temperature at −20. The mixture was stirred until it reached room temperature as the ice bath expired (2 h). The reaction was quenched by the addition of a solution of saturated ammonium chloride. The volume was reduced to ⅓ by evaporating the solvent. The reaction mixture was partioned between ethyl acetate and brine, the aqueous layer was extracted once more with ethyl acetate. The combined organic extracts were washed with water, brine, dried over magnesium sulfate and the resulting liquid was dried at room temperature in vacuo to yield the title compound (24.9 g, 93%). $^1$H NMR (500 MHz, DMSO-$d_6$) δ ppm 0.22 (s, 6H) 0.97 (s, 9H) 4.45 (d, 2H) 5.13 (t, 1H) 6.78 (d, 1H) 7.03 (dd, 1H) 7.38 (d, 1H)

Intermediate 5

[2-(bromomethyl)-5-chlorophenoxy](tert-butyl)dimethylsilane

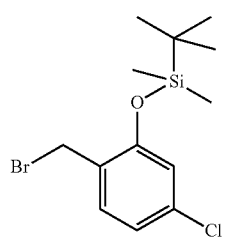 [SMILES: CC(C)(C)[Si](C)(C)Oc1cc(Cl)ccc1CBr]

(2-{[tert-butyl(dimethyl)silyl]oxy}-4-chlorophenyl)methanol (3.72 g, 13.63 mmol) dissolved in DMF (20 mL) added dropwise under 30 min to a cooled 0° C. mixture of bromine (0.734 mL, 14.32 mmol) (+an extra drop to keep a persistent reddish tint to the solution), and triphenylphosphine (3.75 g, 14.32 mmol) in DMF (60 mL), under argon atmosphere. Water was added and the mixture was extracted with EtOAc. The organic phase was washed with 10% aq $Na_2S_2O_2$ solution, dried over MgSO4 and concentrated. Purification by chromatography on silica using gradient elution 20% EtOAc in heptane+0.5% TEA, yielded the title compound (4.4 g, %). $^1$H NMR (500 MHz, CHLORO-FORM-d) δ ppm 0.31-0.35 (m, 6H) 1.04-1.11 (m, 10H) 4.45-4.52 (m, 2H) 6.78-6.85 (m, 1H) 6.90-6.96 (m, 1H) 7.23-7.30 (m, 1H).

Intermediate 6

N-tert-butyl-2-({[2-(6-{[tert-butyl(dimethyl)silyl]oxy}-4-chlorocyclohexa-1,5-dien-1-yl)ethyl]sulfonyl}amino)benzenesulfonamide

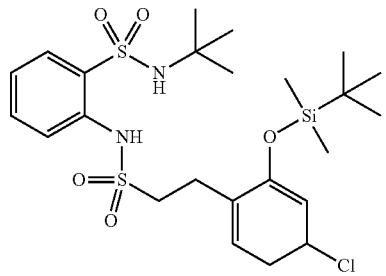 [SMILES: CC(C)(C)NS(=O)(=O)c1ccccc1NS(=O)(=O)CCC1=CCC(Cl)C=C1O[Si](C)(C)C(C)(C)C]

A solution of N-tert-butyl-2-[(methylsulfonyl)amino]benzenesulfonamide (4.56 g, 14.89 mmol) was treated at −78° C. with lithium diisopropylamide (23.83 mL, 47.66 mmol). After 10 minutes a solution of [2-(bromomethyl)-5-chlorophenoxy](tert-butyl)dimethylsilane (5.0 g, 14.89 mmol) in THF (4 mL) was added dropwise under 1 h. The reaction mixture was stirred at −78° C., for 2 h. The reaction mixture was quenched with brine and ethyl acetate was added. The phases were separated and the organic layer was washed with brine, dried over magnesium sulfate, filtered and concentrated under reduced pressure. Purification by chromatography on silica using gradient elution 12-25% EtOAc in heptane to yield the title compound (5.4 g). $^1$H NMR (500 MHz, DMSO-$d_6$) δ ppm 0.10-0.27 (m, 6H) 0.90 (s, 9H) 1.07 (s, 9H) 2.92-3.01 (m, 2H) 3.39-3.52 (m, 2H) 6.78 (d, 1H) 6.96 (dd, 1H) 7.19 (d, 1H) 7.31 (t, 1H) 7.54-7.64 (m, 1H) 7.64-7.70 (m, 1H) 7.88 (d, 1H) 7.99 (s, 1H) 8.77 (s, 1H); MS (ES$^-$) m/z 559, 561.563 [M-H]$^-$.

Intermediate 7

N-tert-butyl-2-({[2-(4-chloro-2-hydroxyphenyl)ethyl]sulfonyl}amino)benzenesulfonamide

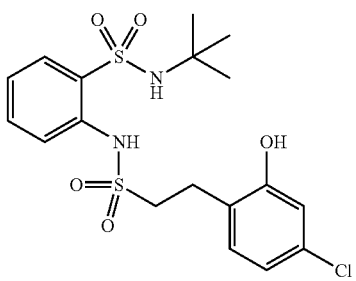 [SMILES: CC(C)(C)NS(=O)(=O)c1ccccc1NS(=O)(=O)CCc1ccc(Cl)cc1O]

Tetrabutylammonium fluoride (1.0 M solution in THF) (0.727 mL, 0.73 mmol) was slowly added to a solution of N-tert-butyl-2-({[2-(4-chloro-2-hydroxyphenyl)ethyl]sulfonyl}amino)benzenesulfonamide (0.340 g, 0.61 mmol) in THF (10 mL) at 0° C. The reaction mixture was stirred for 2 h at 0° C., quenched by addition of sat. brine solution and extracted with ethylacetate. The organic layer was washed with sat. aq. NH4Cl, dried over magnesium sulfate, filtered and concentrated. Purification by chromatography on silica using gradient elution 30-50% EtOAc in heptane yielded the title compound (0.192 g, 71%). $^1$H NMR (500 MHz, DMSO-d$_6$) δ ppm 1.05-1.15 (m, 11H) 2.89-2.96 (m, 2H) 3.46-3.54 (m, 2H) 6.75 (dd, 1H) 6.77 (d, 1H) 7.08 (d, 1H) 7.30 (t, 1H) 7.55-7.65 (m, 1H) 7.65-7.73 (m, 1H) 7.89 (d, 1H) 8.02 (s, 1H) 8.78 (s, 1H) 10.04 (s, 1H); MS (ES$^-$) m/z 445, 447, 449 [M-H]$^-$.

Intermediate 8

2-(2-cyanophenyl)ethyl Methanesulfonate

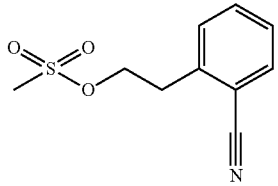

Methanesulfonyl chloride (0.184 ml, 2.38 mmol) was added to a cold 0° C. solution of 2-(2-hydroxyethyl)benzonitrile (0.175 g, 1.19 mmol) and triethylamine (0.380 ml, 2.73 mmol) in dichloromethane (10 ml) and the reaction mixture was stirred over night at room temperature. The reaction mixture was washed with water and sat aq Na2CO3 solution, dried over MgSO4 and concentrated, to yield the title compound (0.327 g, 122%). The title compound was used in the next step without further purification. $^1$H NMR (500 MHz, CHLOROFORM-d) δ ppm 2.98 (s, 3H) 3.31 (t, 2H) 4.51 (t, 2H) 7.38-7.46 (m, 2H) 7.59 (td, 1H) 7.69 (dd, 1H).

Intermediate 9

2-(1-methyl-1H-indol-4-yl)ethyl Methanesulfonate

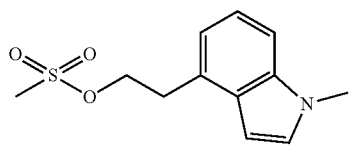

Methanesulfonyl chloride (0.208 ml, 2.69 mmol) was added to a cold 0° C. solution of 2-(1-methyl-1H-indol-4-yl)ethanol (0.236 g, 1.35 mmol) and triethylamine (0.431 ml, 3.10 mmol) in dichloromethane (10 ml). The reaction mixture was allowed to reach room temperature and stirred for 3 h. The reaction mixture was washed with water and sat. aq. Na$_2$CO$_3$ solution, dried over MgSO4 and the solvent was removed under reduced pressure to yield the title compound (0.348 g) (102%), and used in the next step without further purification.

$^1$H NMR (500 MHz, CHLOROFORM-d) δ ppm 2.75 (s, 3H) 3.36 (t, 2H) 3.81 (s, 3H) 4.55 (t, 2H) 6.51-6.56 (m, 1H) 6.99 (d, 1H) 7.10 (d, 1H) 7.15-7.22 (m, 1H) 7.24-7.27 (m, 1H).

Intermediate 10

N-tert-butyl-2-[({2-[4-chloro-2-(2-phenylethoxy)phenyl]ethyl}sulfonyl)amino]benzenesulfonamide

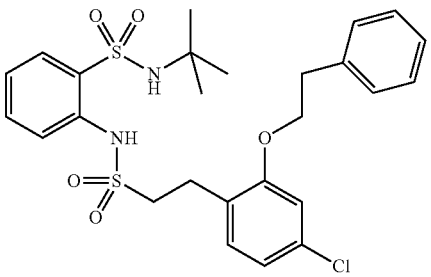 [SMILES: CC(C)(C)NS(=O)(=O)c1ccccc1NS(=O)(=O)CCc1ccc(Cl)cc1OCCc1ccccc1]

Potassium carbonate (0.038 g, 0.28 mmol) and (2-bromoethyl)benzene (0.021 mL, 0.15 mmol) were added to a solution of N-tert-butyl-2-({[2-(4-chloro-2-hydroxyphenyl)ethyl]sulfonyl}-amino)benzenesulfonamide (0.062 g, 0.14 mmol) in DMF (5 mL) at r.t. The reaction was stirred over night. Additional (2-bromoethyl)benzene (0.021 mL, 0.15 mmol) and potassium carbonate (0.042 g, 0.31 mmol) was added and the reaction mixture was stirred for 5 days at r.t. Another portion of (2-bromoethyl)benzene (0.120 mL, 0.14 mmol) was added and the reaction mixture was stirred over night. Heating of the reaction mixture at 50° C. over night, then heated at 90° C. for 5 h followed by cooling to room temperature. The product mixture was later pooled with a second batch, starting from potassium carbonate (0.088 g, 0.63 mmol) and (2-bromoethyl)benzene (0.077 ml, 0.56 mmol), which were added to a solution of N-tert-butyl-2-({[2-(4-chloro-2-hydroxyphenyl)ethyl]sulfonyl}amino)benzenesulfonamide (0.063 g, 0.14 mmol) in DMF (5 ml) at r.t. The reaction was stirred at 50° over night, heated at 90° C. for 5 h then cooled to room temperature. The two batches were pooled, filtered through a plug of celite. The filtrate was washed with ethylacetate and concentrated under reduced pressure. Purification by chromatography on silica using gradient elution 25-33% EtOAc in heptane yielded the title compound (59.2 mg, 38%). $^1$H NMR (500 MHz, DMSO-d$_6$) δ ppm 1.08-1.15 (m, 10H) 2.82-2.97 (m, 4H) 3.41-3.48 (m, 2H) 4.12 (t, 2H) 6.89 (dd, 1H) 7.00 (d, 1H) 7.13 (d, 1H) 7.17-7.22 (m, 1H) 7.24-7.33 (m, 5H) 7.57-7.64 (m, 1H) 7.64-7.71 (m, 1H) 7.89 (dd, 1H) 8.04 (s, 1H) 8.80 (s, 1H); MS (ES$^-$) m/z 549, 551, 553 [M-H]$^-$.

Intermediate 11

N-tert-butyl-2-{[(2-{4-chloro-2-[2-(2-methoxyphenyl)ethoxy]phenyl}ethyl)sulfonyl]amino}benzenesulfonamide

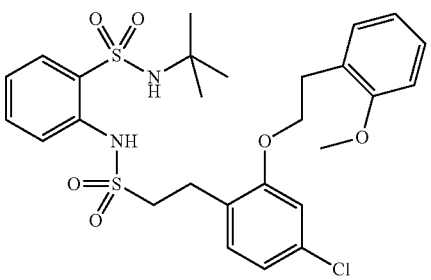 [SMILES: COc1ccccc1CCOc1cc(Cl)ccc1CCS(=O)(=O)Nc1ccccc1S(=O)(=O)NC(C)(C)C]

A microwave vial was charged with N-tert-butyl-2-({[2-(4-chloro-2-hydroxyphenyl)-ethyl]sulfonyl}amino)benzenesulfonamide (206 mg, 0.46 mmol), cesium carbonate (300 mg, 0.92 mmol), 2-methoxyphenethyl bromide (0.146 mL, 0.92 mmol) and N,N-dimethylformamide (3 mL). The vial was capped and heated in the microwave oven at 110° C. for 30 min. More cesium carbonate (300 mg, 0.92 mmol) and 2-methoxyphenethyl bromide (0.146 mL, 0.92 mmol) were added and the mixture was heated for 30 min at 110° C. using MW. Water was added and the mixture was extracted twice with ethyl acetate. The combined organic extracts were washed with ½ saturated brine, brine, dried over magnesium sulfate, filtered and the solvent was evaporated. Purification by preparative HPLC gave the title compound (78 mg, 29.1%); MS (ES⁻) m/z 579, 581 [M-H]⁻.

Intermediate 12

N-tert-butyl-2-{[(2-{4-chloro-2-[2-(3-methoxyphenyl)ethoxy]phenyl}ethyl)sulfonyl]amino}benzenesulfonamide

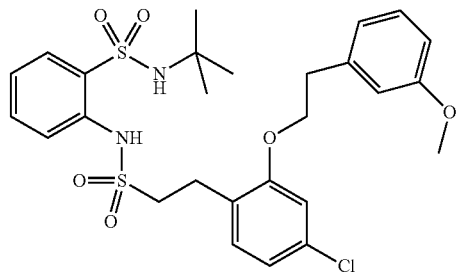 [SMILES: COc1cccc(CCOc2cc(Cl)ccc2CCS(=O)(=O)Nc2ccccc2S(=O)(=O)NC(C)(C)C)c1]

A microwave vial was charged with N-tert-butyl-2-({[2-(4-chloro-2-hydroxyphenyl)ethyl]-sulfonyl}amino)benzenesulfonamide (203 mg, 0.45 mmol), cesium carbonate (296 mg, 0.91 mmol), 3-methoxyphenethyl bromide (0.143 mL, 0.91 mmol) and N,N-dimethylformamide (3 mL). The vial was capped and heated using MW at 110° C. for 3 h. Additional cesium carbonate (296 mg, 0.91 mmol) was added and the mixture was heated for 2 h at 110° C. in the MW. An additional 2 eq of 3-methoxyphenethyl bromide (0.143 mL, 0.91 mmol) was added and the mixture was heated at 110° C. for 30 min. Water was added and the mixture was extracted twice with ethyl acetate. The combined organic extracts were washed with ½ saturated brine, brine, dried over magnesium sulfate, filtered and the solvent was evaporated under reduced pressure. Purification by preparative HPLC gave the title compound (62.0 mg, 23.49%); MS (ES⁻) m/z 579, 581 [M-H]⁻.

Intermediate 13

N-tert-butyl-2-{[(2-{4-chloro-2-[2-(4-methoxyphenyl)ethoxy]phenyl}ethyl)sulfonyl]amino}benzenesulfonamide

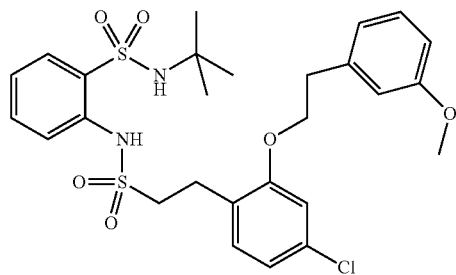 [SMILES: COc1cccc(CCOc2cc(Cl)ccc2CCS(=O)(=O)Nc2ccccc2S(=O)(=O)NC(C)(C)C)c1]

N-tert-butyl-2-({[2-(4-chloro-2-hydroxyphenyl)ethyl]sulfonyl}amino)benzenesulfonamide (0.451 g, 1.01 mmol) and 4-methoxyphenethyl methanesulfonate [CAS 73735-36-1] (0.325 g, 1.41 mmol) was dissolved in acetonitrile (10 ml) and Potassium carbonate (0.195 g, 1.41 mmol) was added. The mixture was stirred over night at 75° C. The solvent was evaporated, the crude diluted with EtOAc and the organic phase was washed with Brine, dried over MgSO4 and concentrated. Purification by chromatography on silica using gradient elution 12-50% EtOAc in heptane yielded the title compound (0.207 g, 35%). ¹H NMR (500 MHz, DMSO-d₆) δ ppm 1.10 (s, 9H) 2.80 (t, 2H) 2.87-2.98 (m, 2H) 3.40-3.51 (m, 2H) 3.65-3.75 (m, 3H) 4.07 (t, 2H) 6.77-6.86 (m, 2H) 6.88 (dd, 1H) 6.99 (d, 1H) 7.13 (d, 1H) 7.17 (d, 2H) 7.29 (t, 1H) 7.56-7.64 (m, 1H) 7.65-7.71 (m, 1H) 7.89 (d, 1H) 8.04 (s, 1H) 8.81 (s, 1H); MS (ES⁻) m/z 579, 581, 583 [M-H]⁻.

Intermediate 14

N-tert-butyl-2-{[(2-{4-chloro-2-[2-(2-cyanophenyl)ethoxy]phenyl}ethyl)sulfonyl]amino}benzenesulfonamide

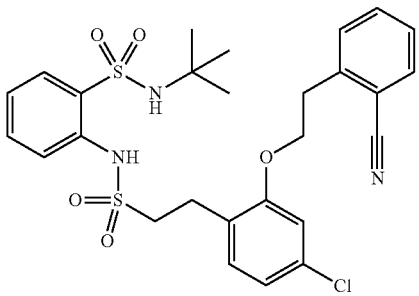 [SMILES: CC(C)(C)NS(=O)(=O)c1ccccc1NS(=O)(=O)CCc1ccc(Cl)cc1OCCc1ccccc1C#N]

The title compound was prepared following the procedure for Intermediate 13 above, starting from N-tert-butyl-2-({[2-(4-chloro-2-hydroxyphenyl)ethyl]sulfonyl}amino)benzenesulfonamide (0.322 g, 0.72 mmol) and 2-cyanophenethyl methanesulfonate (0.325 g, 1.44 mmol) in acetonitrile (10 ml) and potassium carbonate (0.140 g, 1.01 mmol). Purification by chromatography on silica using gradient elution 12-50% EtOAc in heptane yielded the title compound (0.039 g, 9.5%). ¹H NMR (500 MHz, DMSO-d₆) δ ppm 1.04-1.14 (m, 9H) 2.85-2.97 (m, 2H) 3.15 (t, 2H) 3.37-3.44 (m, 2H) 4.22 (t, 2H) 6.90 (dd, 1H) 7.03-7.07 (m, 1H) 7.13 (s, 1H) 7.25-7.34 (m, 1H) 7.42 (td, 1H) 7.55 (d, 1H) 7.58-7.66 (m, 3H) 7.79 (dd, 1H) 7.88 (d, 1H) 8.02 (s, 1H) 8.78 (s, 1H); MS (ES⁻) m/z 547, 576, 578 [M-H]⁻.

Intermediate 15

N-tert-butyl-2-{[(2-{4-chloro-2-[2-(3-cyanophenyl)ethoxy]phenyl}ethyl)sulfonyl]amino}benzenesulfonamide

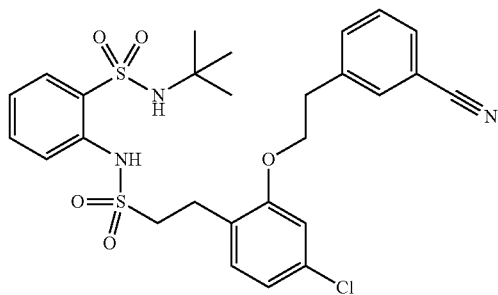 [SMILES: CC(C)(C)NS(=O)(=O)c1ccccc1NS(=O)(=O)CCc1ccc(Cl)cc1OCCc1cccc(C#N)c1]

The title compound was prepared following the procedure for Intermediate 13 above, starting from N-tert-butyl-2-({[2-(4-chloro-2-hydroxyphenyl)ethyl]sulfonyl}amino)benzenesulfonamide (0.357 g, 0.80 mmol) and 3-cyanophenethyl methanesulfonate [CAS 655250-92-3] (0.360 g, 1.6 mmol) were dissolved in acetonitrile (10 ml) and potassium carbonate (0.155 g, 1.12 mmol) Purification by chromatography on silica using gradient elution 12-50% EtOAc in heptane yielded the title compound (0.081 g, 17.6%). NMR very difficult to analyze MS (ES⁻) m/z 547, 576, 578 [M-H]⁻.

Intermediate 16

N-tert-butyl-2-{[(2-{4-chloro-2-[2-(4-cyanophenyl)ethoxy]phenyl}ethyl)sulfonyl]amino}benzenesulfonamide

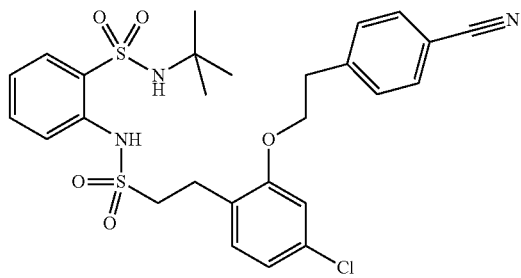 [SMILES: CC(C)(C)NS(=O)(=O)c1ccccc1NS(=O)(=O)CCc1ccc(Cl)cc1OCCc1ccc(C#N)cc1]

N-tert-butyl-2-({[2-(4-chloro-2-hydroxyphenyl)ethyl]sulfonyl}amino)benzenesulfonamide (0.3 g, 0.67 mmol) and 2-(4-cyanophenyl)ethyl methanesulfonate [CAS 119744-42-2] (0.227 g, 1.01 mmol) was dissolved in acetonitrile (10 mL) and potassium carbonate (0.139 g, 1.01 mmol) was added. The mixture was stirred over night at 75° C. More 4-cyanophenethyl methanesulfonate (0.57 g, 2.53 mmol) in acetonitrile (1 mL) and heating was continued for 6 h. Reaction was heated to 100° C. for 6 h. The solvent was diluted with EtOAc and the organic phase was washed with brine, dried over MgSO4 and concentrated. Purification by chromatography on silica using gradient elution 0-50% EtOAc in heptane, yielded the title compound (0.257 g 66.5%); MS (ES⁻) m/z 574, 576, 577 [M-H]⁻. MS (ES-) m/z 574 [M-H]⁻

Intermediate 17

N-tert-butyl-2-{[(2-{4-chloro-2-[2-(1-methyl-1H-indol-4-yl)ethoxy]phenyl}ethyl)sulfonyl]amino}benzenesulfonamide

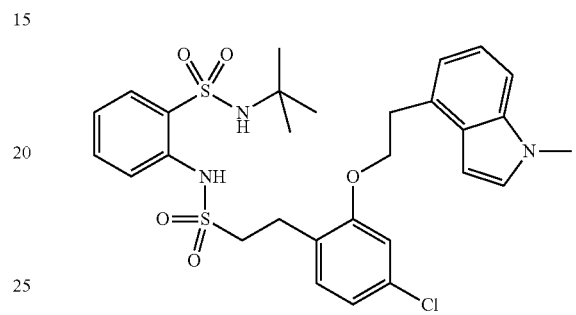

N-tert-butyl-2-({[2-(4-chloro-2-hydroxyphenyl)ethyl]sulfonyl}amino)benzenesulfonamide (0.243 g, 0.54 mmol) and 2-(1-methyl-1H-indol-4-yl)ethyl methanesulfonate (0.345 g, 1.36 mmol) was dissolved in acetonitrile (10 ml) and potassium carbonate (0.105 g, 0.76 mmol) was added. The mixture was stirred over night at 75° C. The solvent was evaporated under reduced pressure, the crude product was diluted with EtOAc and the organic phase was washed with brine, dried over MgSO4 and concentrated. Purification by chromatography on silica using gradient elution 17-50% EtOAc in heptane, yielded the title compound (0.103 g, 31%). MS (ES⁻) m/z 602, 604, 606 [M-H]⁻.

Intermediate 18

N-tert-butyl-2-{[(2-{4-chloro-2-[2-(2-oxo-2,3-dihydro-1H-indol-4-yl)ethoxy]phenyl}ethyl)sulfonyl]amino}benzenesulfonamide

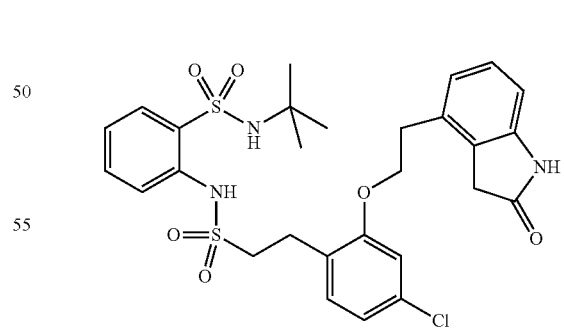

N-tert-butyl-2-({[2-(4-chloro-2-hydroxyphenyl)ethyl]sulfonyl}amino)benzenesulfone (273 mg, 0.61 mmol) and 2-(2-oxo-2,3-dihydro-1H-indol-4-yl)ethyl methanesulfonate [CAS 139122-21-7](0.273 g, 0.61 mmol) was dissolved in acetonitrile (10 mL) and potassium carbonate (0.234 g, 0.92 mmol) was added. The mixture was stirred over night at 75° C. Reaction was heated for 6 h. The temperature was elevated to 100° C. and heating was continued for 6 h. The reaction mixture was diluted with EtOAc and the organic phase was washed with brine, dried over MgSO4 and concentrated under reduced pressure. Purification by chromatography on silica using gradient elution 0-50% EtOAc in heptane, yielded the title compound (0.060 g, 16%). $^1$H NMR (500 MHz, DMSO-$d_6$) δ ppm 1.11 (s, 9H), 2.82 (t, J=6.78 Hz, 2H), 2.91-2.98 (m, 2H), 3.44-3.55 (m, 4H), 4.14 (t, J=6.78 Hz, 2H), 6.68 (d, J=7.57 Hz, 1H), 6.84 (d, J=7.57 Hz, 1H), 6.90 (dd, J=8.20, 1.89 Hz, 1H), 7.03 (d, J=1.89 Hz, 1H), 7.05-7.18 (m, 2H), 7.30 (t, J=7.57 Hz, 1H), 7.59-7.70 (m, 2H), 7.90 (dd, J=7.88, 1.26 Hz, 1H), 8.05 (s, 1H), 8.81 (s, 1H), 10.36 (s, 1H); MS (ES$^-$) m/z 604, 606, 607 [M-H]$^-$

Example 1

2-(2-(4-chloro-2-phenethoxyphenyl)ethylsulfonamido)benzenesulfonamide

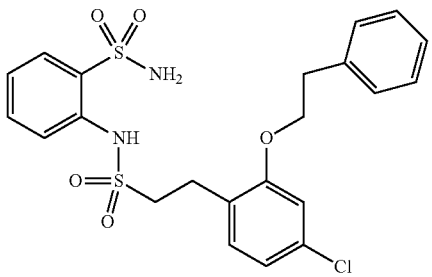 [SMILES: NS(=O)(=O)c1ccccc1NS(=O)(=O)CCc1ccc(Cl)cc1OCCc1ccccc1]

N-tert-butyl-2-(2-(4-chloro-2-phenethoxyphenyl)ethylsulfonamido)benzenesulfonamide (0.058 g, 0.11 mmol) was dissolved in 2,2,2-trifluoroacetic acid (1.5 ml, 19.47 mmol) and stirred for 5 h. The reaction mixture was co-evaporated with toluene, Purification by preparative HPLC gave the title compound (0.033 g 64%). $^1$H NMR (500 MHz, DMSO-$d_6$) δ ppm 2.84-2.98 (m, 4H) 3.37-3.46 (m, 2H) 4.13 (t, 2H) 6.88 (dd, 1H) 7.00 (d, 1H) 7.13 (d, 1H) 7.17-7.24 (m, 1H) 7.24-7.36 (m, 5H) 7.55-7.69 (m, 2H) 7.81-7.95 (m, 3H) 8.95 (s, 1H); MS (ES$^-$) m/z 493, 495, 497 [M-H]$^-$.

Example 2

2-(2-(4-chloro-2-(2-methoxyphenethoxy)phenyl)ethylsulfonamido)benzenesulfonamide

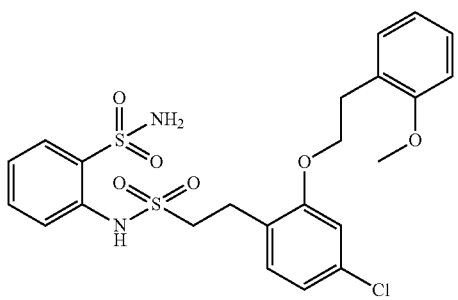 [SMILES: COc1ccccc1CCOc1cc(Cl)ccc1CCS(=O)(=O)Nc1ccccc1S(N)(=O)=O]

To N-tert-butyl-2-(2-(4-chloro-2-(2-methoxyphenethoxy)phenyl)ethylsulfonamido)benzenesulfonamide (77 mg, 0.13 mmol) trifluoroacetic acid (1 mL, 13.06 mmol) was added and the mixture was stirred at room temperature for 2 h. The solvent was evaporated followed by co-evaporation with toluene (1 mL). Purification by preparative HPLC gave the title compound (39.0 mg, 56.1%). $^1$H NMR (500 MHz, DMSO-$d_6$) δ ppm 2.84-2.94 (m, 4H) 3.43 (m, 2H) 3.81 (s, 3H) 4.05 (t, 2H) 6.83-6.90 (m, 2H) 6.96 (d, 1H) 7.03 (d, 1H) 7.13 (d, 1H) 7.21 (m, 2H) 7.31 (t, 1H) 7.57-7.66 (m, 2H) 7.84 (s, 2H) 7.88 (d, 1H) 8.95 (s, 1H); MS (ES$^-$) m/z 523, 525 [M-H]$^-$.

Example 3

2-(2-(4-chloro-2-(3-methoxyphenethoxy)phenyl)ethylsulfonamido)benzenesulfonamide

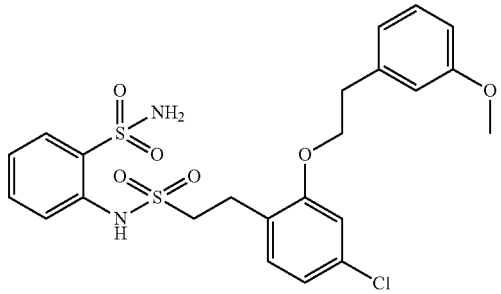 [SMILES: COc1cccc(CCOc2cc(Cl)ccc2CCS(=O)(=O)Nc2ccccc2S(N)(=O)=O)c1]

To N-tert-butyl-2-(2-(4-chloro-2-(3-methoxyphenethoxy)phenyl)ethylsulfonamido)benzenesulfonamide (61 mg, 0.10 mmol) was trifluoroacetic acid (1 mL, 13.06 mmol) added and the mixture was stirred at room temperature for 2 h. The solvent was evaporated followed by co-evaporation with methanol. Purification by preparative HPLC gave the title compound (32.0 mg, 58.1%). $^1$H NMR (500 MHz, DMSO-$d_6$) δ ppm 2.85 (t, 2H) 2.92 (m, 2H) 3.42 (m, 2H) 3.73 (s, 3H) 4.13 (t, 2H) 6.77 (dd, 1H) 6.82-6.90 (m, 3H) 7.00 (d, 1H) 7.14 (d, 1H) 7.18 (t, 1H) 7.30 (t, 1H) 7.57-7.65 (m, 2H) 7.83-7.90 (m, 3H) 8.94 (s, 1H); MS (ES$^-$) m/z 523, 525 [M-H]$^-$.

Example 4

2-(2-(4-chloro-2-(4-methoxyphenethoxy)phenyl)ethylsulfonamido)benzenesulfonamide

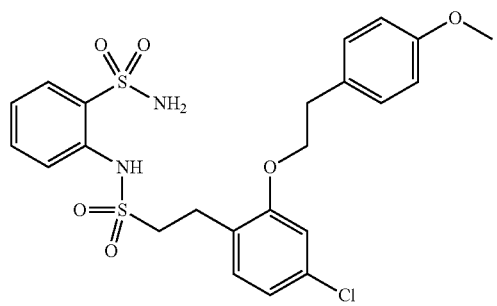 [SMILES: COc1ccc(CCOc2cc(Cl)ccc2CCS(=O)(=O)Nc2ccccc2S(N)(=O)=O)cc1]

N-tert-butyl-2-(2-(4-chloro-2-(4-methoxyphenethoxy)phenyl)ethylsulfonamido)benzenesulfonamide (0.207 g, 0.36 mmol) was dissolved in trifluoroacetic acid (1.5 mL, 19.47 mmol) and stirred for 3 h. The reaction mixture was co-evaporated with toluene. Purification by preparative HPLC gave the title compound (0.079 g, 42%). $^1$H NMR (500 MHz, DMSO-d$_6$) δ ppm 1.99 (t, 2H) 2.04-2.14 (m, 2H) 2.60 (br. s., 2H) 2.88 (s, 3H) 3.24 (t, 2H) 5.98-6.08 (m, 3H) 6.15 (d, 1H) 6.30 (d, 1H) 6.35 (d, 2H) 6.43-6.55 (m, 1H) 6.78 (d, 1H) 6.79-6.87 (m, 1H) 6.97-7.10 (m, 3H) 8.13 (s, 1H); MS (ES$^-$) m/z 523, 525, 527 [M-H]$^-$.

Example 5

2-(2-(4-chloro-2-(2-cyanophenethoxy)phenyl)ethylsulfonamido)benzenesulfonamide

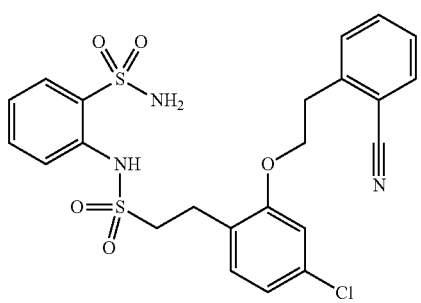 [SMILES: N#Cc1ccccc1CCOc1cc(Cl)ccc1CCS(=O)(=O)Nc1ccccc1S(N)(=O)=O]

N-tert-butyl-2-(2-(4-chloro-2-(2-cyanophenethoxy)phenyl)ethylsulfonamido)benzenesulfonamide (37.0 mg, 0.06 mmol) was dissolved in trifluoroacetic acid (1.5 ml, 19.47 mmol) and stirred for 4 h. The reaction mixture was coevaporated with toluene. Purification by preparative HPLC gave the title compound (0.020 g, 59%). $^1$H NMR (500 MHz, DMSO-d$_6$) δ ppm 2.83-2.95 (m, 2H) 3.14-3.19 (m, 2H) 3.35 (br. s., 2H) 4.23 (t, 2H) 6.89 (dd, 1H) 7.01-7.17 (m, 2H) 7.30 (br. s., 1H) 7.41 (td, 1H) 7.51-7.67 (m, 4H) 7.78 (dd, 1H) 7.80-7.93 (m, 3H) 8.92 (s, 1H); m/z 518, 520, 522 [M-H]$^-$.

Example 6

2-(2-(4-chloro-2-(3-cyanophenethoxy)phenyl)ethylsulfonamido)benzenesulfonamide

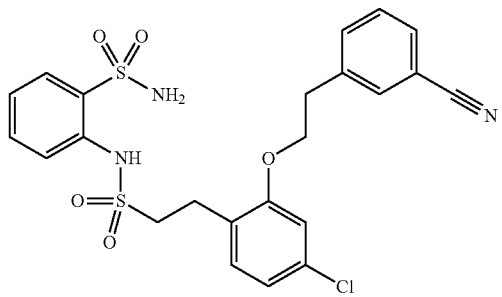 [SMILES: N#Cc1cccc(CCOc2cc(Cl)ccc2CCS(=O)(=O)Nc2ccccc2S(N)(=O)=O)c1]

N-tert-butyl-2-(2-(4-chloro-2-(3-cyanophenethoxy)phenyl)ethylsulfonamido)benzenesulfonamide (0.079 g, 0.14 mmol) was dissolved in trifluoroacetic acid (1.5 ml, 19.47 mmol) and stirred for 4 h. The reaction mixture was co-evaporated with toluene. Purification of the crude by prep. HPLC gave (0.025 g, 36%). $^1$H NMR (500 MHz, DMSO-d$_6$) δ ppm 2.83-2.92 (m, 2H) 2.96 (t, 2H) 3.36-3.44 (m, 2H) 4.18 (t, 2H) 6.89 (dd, 1H) 7.02 (d, 1H) 7.13 (d, 1H) 7.30 (t, 1H) 7.44-7.52 (m, 1H) 7.57-7.65 (m, 3H) 7.68 (d, 1H) 7.78 (s, 1H) 7.81-7.94 (m, 3H) 8.93 (s, 1H); MS (ES$^-$) m/z 518, 520, 522 [M-H]$^-$.

Example 7

2-(2-(4-chloro-2-(4-cyanophenethoxy)phenyl)ethylsulfonamido)benzenesulfonamide

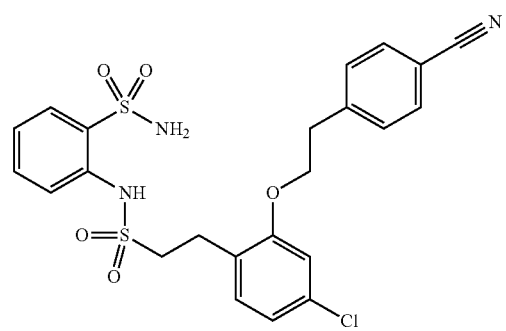 [SMILES: N#Cc1ccc(CCOc2cc(Cl)ccc2CCS(=O)(=O)Nc2ccccc2S(N)(=O)=O)cc1]

Trifluoroacetic acid (1 mL, 0.45 mmol) was added to N-tert-butyl-2-(2-(4-chloro-2-(4-cyanophenethoxy)phenyl)ethylsulfonamido)benzenesulfonamide (0.257 g, 0.45 mmol) and the mixture was stirred for 2 h and then evaporated. Purification by preparative HPLC gave the title compound (0.042 g, 18%). $^1$H NMR (500 MHz, DMSO-d$_6$) δ ppm 2.83-2.91 (m, 2H), 3.00 (t, J=6.31 Hz, 2H), 3.35-3.43 (m, 2H), 4.18 (t, J=6.46 Hz, 2H), 6.89 (dd, J=7.88, 1.89 Hz, 1H), 7.01 (d, J=1.58 Hz, 1H), 7.12 (d, J=8.20 Hz, 1H), 7.31 (t, J=7.25 Hz, 1H), 7.48 (d, J=7.88 Hz, 2H), 7.57-7.68 (m, 2H), 7.74 (d, J=8.20 Hz, 2H), 7.81-7.92 (m, 3H), 8.95 (s, 1H); MS (ES$^-$) m/z 518, 520, 521 [M-H]$^-$

Example 8

2-(2-(4-chloro-2-(2-(1-methyl-1H-indol-4-yl)ethoxy)phenyl)ethylsulfonamido)benzenesulfonamide

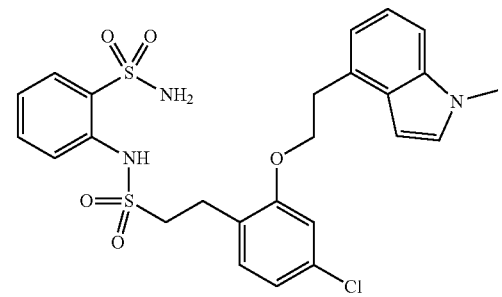 [SMILES: Cn1ccc2c(CCOc3cc(Cl)ccc3CCS(=O)(=O)Nc3ccccc3S(N)(=O)=O)cccc21]

N-tert-butyl-2-(2-(4-chloro-2-(2-(1-methyl-1H-indol-4-yl)ethoxy)phenyl)ethylsulfonamido)-benzenesulfonamide (0.100 g, 0.17 mmol) was dissolved in trifluoroacetic acid (1.5 mL, 19.47 mmol) and stirred for 3 h. Purification by preparative HPLC gave the title compound (0.033 g, 36%). $^1$H NMR (500 MHz, DMSO-d$_6$) δ ppm 2.85-2.95 (m, 2H) 3.09-3.21 (m, 2H) 3.35-3.45 (m, 2H) 3.76 (s, 3H) 4.19 (t, 2H) 6.49 (d, 1H) 6.86 (dd, 1H) 6.90-6.98 (m, 2H) 7.06 (t, 1H) 7.11 (d, 1H) 7.23-7.37 (m, 3H) 7.51-7.66 (m, 2H) 7.76-7.96 (m, 3H) 8.93 (m 1H); MS (ES⁻) m/z 546, 548, 550 [M-H]⁻.

Example 9

2-(2-(4-chloro-2-(2-(2-oxoindolin-4-yl)ethoxy)phenyl)ethylsulfonamido)benzenesulfonamide

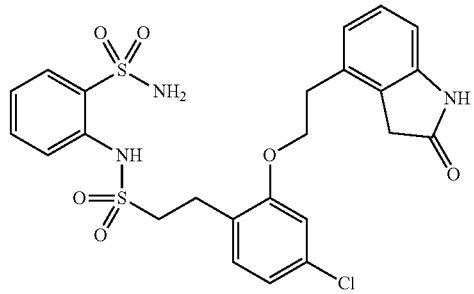 [SMILES: NS(=O)(=O)c1ccccc1NS(=O)(=O)CCc1ccc(Cl)cc1OCCc1cccc2c1CC(=O)N2]

Trifluoroacetic acid (1 mL, 0.10 mmol) was added to N-tert-butyl-2-(2-(4-chloro-2-(2-(2-oxoindolin-4-yl)ethoxy)phenyl)ethylsulfonamido)benzenesulfonamide (60.6 mg, 0.10 mmol) and the mixture was stirred for 2 h and then evaporated. Purification by preparative HPLC gave the title compound (0.029 g, 53%). ¹H NMR (500 MHz, DMSO-d₆) δ ppm 2.84 (t, J=6.78 Hz, 2H), 2.88-2.98 (m, 2H), 3.40-3.48 (m, 2H), 3.50 (s, 2H), 4.15 (t, J=6.94 Hz, 2H), 6.68 (d, J=7.57 Hz, 1H), 6.85 (d, J=7.88 Hz, 1H), 6.90 (dd, J=8.20, 1.89 Hz, 1H), 7.03 (d, J=1.89 Hz, 1H), 7.09 (t, J=7.72 Hz, 1H), 7.15 (d, J=8.20 Hz, 1H), 7.32 (t, J=7.57 Hz, 1H), 7.57-7.70 (m, 2H), 7.80-7.97 (m, 3H), 8.96 (s, 1H), 10.36 (s, 1H); MS (ES⁻) m/z 548, 550 [M-H]⁻.

Intermediate 19

3-(benzylsulfanyl)-4-nitrophenyl]methanol

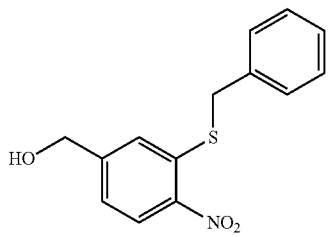 [SMILES: O=[N+]([O-])c1ccc(CO)cc1SCc1ccccc1]

Diisopropylethylamine (72 mL, 584 mmol) and benzyl mercaptan (39.87 g, 321 mmol) were added to a stirred solution of (3-fluoro-4-nitrophenyl)methanol (50 g, 292 mmol) in DMSO (250 mL). The reaction mixture was heated at 80° C. for 3 h, then cooled to room temperature, and poured into ice-water. The precipitated solid was collected by filtration, washed with water and dried under reduced pressure to yield the title compound (87 g, 108%). ¹H NMR (400 MHz, CHLOROFORM-d) δ 4.20 (s, 2H) 4.73 (d, J=4.8 Hz, 2H) 7.30 (m, 4H) 7.43 (m, 2H) 7.53 (d, J=8 Hz, 1H) 8.21 (s, 1H).

Intermediate 20

{[3-(benzylsulfanyl)-4-nitrobenzyl]oxy}(tert-butyl)diphenylsilane

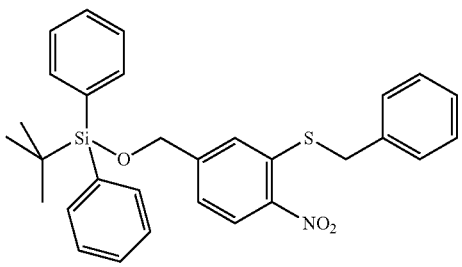 [SMILES: CC(C)(C)[Si](OCc1ccc([N+](=O)[O-])c(SCc2ccccc2)c1)(c1ccccc1)c1ccccc1]

A mixture of [3-(benzylsulfanyl)-4-nitrophenyl]methanol (87 g, 316 mmol), tert-butyldiphenylchlorosilane (86.86 g, 316 mmol) and imidazole (43.03 g, 632 mmol) in dry DMF (550 mL) was stirred at room temperature overnight. The reaction mixture was partitioned between water (500 mL) and ethyl acetate (2000 mL). The organic phase was separated, washed with brine (3×500 mL), dried over anhydrous sodium sulfate and concentrated under reduced pressure. Purification by chromatography on silica using gradient elution 5-10% EtOAc in heptane, yielded the title compound (148 g, 99%). ¹H NMR (400 MHz, CHLOROFORM-d) δ ppm 1.10 (s, 9H) 4.20 (s, 2H) 4.74 (s, 2H) 7.29-7.48 (m, 13H) 7.65 (d, J=8 Hz, 4H) 8.13 (s, 1H)

Intermediate 21

5-({[tert-butyl(diphenyl)silyl]oxy}methyl)-2-nitrobenzenesulfonyl Chloride

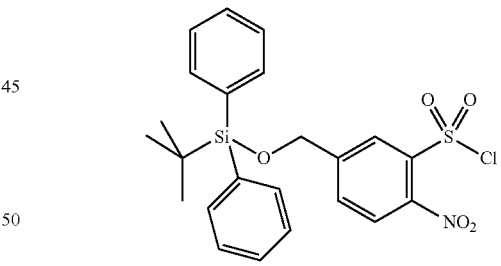

To a stirred solution of {[3-(benzylsulfanyl)-4-nitrobenzyl]oxy}(tert-butyl)diphenylsilane (10 g, 19.67 mmol) in dichloromethane (600 mL) were added formic acid (300 mL) and a solution of sodium chloride (18 g, 305.58 mmol) in water (300 mL). N-Chlorosuccinimide (24 g, 179.07 mmol) was then added in portions and the resulting mixture was stirred vigorously for about 1 hour until all starting material was consumed. The organic phase was separated, dried over anhydrous sodium sulfate and concentrated under reduced pressure to yield the title compound (10.2 g, 105%), which was used in the next step without further purification. ¹H NMR (400 MHz, CHLOROFORM-d) δ ppm 1.12 (s, 9H) 4.87 (s, 2H) 7.43 (m, 6H) 7.64 (d, J=8 Hz, 4H) 7.74 (d, J=8 Hz, 1H) 7.81 (s, 1H) 8.18 (d, J=8 Hz, 1H)

Intermediate 22 iv) N-(tert-Butyl)-5-(((tert-butyldiphenylsilyl)oxy)methyl)-2-nitrobenzene-sulfonamide

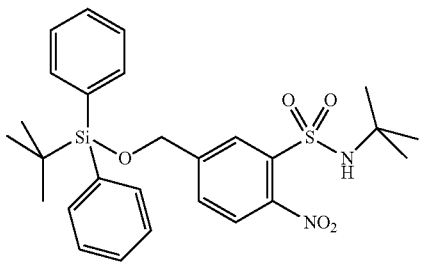 [SMILES: CC(C)(C)NS(=O)(=O)c1cc(CO[Si](c2ccccc2)(c2ccccc2)C(C)(C)C)ccc1[N+](=O)[O-]]

Tert-Butylamine (36.5 mL, 346 mmol) was added dropwise to a stirred solution of 5-({[tert-butyl(diphenyl)silyl]oxy}methyl)-2-nitrobenzenesulfonyl chloride 4 (36.5 g, crude) in DCM (300 mL) at room temperature. The resulting mixture was stirred overnight and then water (250 mL) was added. The organic layer was separated, dried over anhydrous sodium sulfate and concentrated under reduced pressure. Purification by chromatography on silica using gradient elution 4-12% EtOAc in heptanes, to yield the title compound (18.9 g, 48% over two steps from {[3-(benzylsulfanyl)-4-nitrobenzyl]oxy}(tert-butyl)diphenylsilane (Intermediate 21)). $^1$H NMR (400 MHz, Methanol-$d_4$) δ ppm 1.10 (s, 9H) 4.90 (s, 2H) 7.42 (m, 6H) 7.66 (d, J=8 Hz, 4H) 7.74 (d, J=8 Hz, 1H) 7.80 (s, 1H) 8.05 (d, J=8 Hz, 1H).

Intermediate 23

2-amino-N-tert-butyl-5-({[tert-butyl(diphenyl)silyl]oxy}methyl)benzenesulfonamide

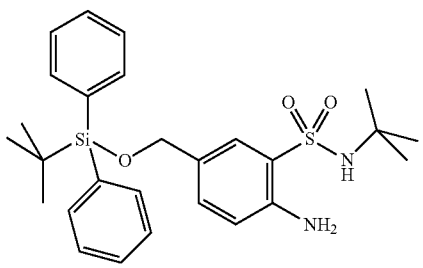 [SMILES: CC(C)(C)NS(=O)(=O)c1cc(CO[Si](c2ccccc2)(c2ccccc2)C(C)(C)C)ccc1N]

To a stirred solution of N-(tert-Butyl)-5-(((tert-butyldiphenylsilyl)oxy)methyl)-2-nitrobenzene-sulfonamide (4.61 g, 8.75 mmol) was added ammonium chloride (2.34 g, 43.75 mmol) followed by zinc dust (4.61 g, 96 mmol). The reaction mixture was heated to reflux for 2 hours, then cooled to room temperature and filtered through a pad of Celite. The filtrate was concentrated under reduced pressure and the residue was partitioned between dichloromethane (100 mL) and water (50 mL). The organic layer was separated, washed with brine (50 mL), dried over anhydrous sodium sulfate and concentrated under reduce pressure to yield the title compound (4.3 g, 99%). $^1$H NMR (400 MHz, CHLOROFORM-d) δ ppm 1.07 (s, 9H) 1.19 (s, 9H) 4.65 (s, 2H) 4.69 (s, 1H) 4.74 (s. 2H) 6.71 (d, J=8.00 Hz, 1H) 7.26 (dd, J=8.00, 2.00 Hz, 1H) 7.39 (m, 6H) 7.67 (m, 4H) 7.73 (d, J=2.00 Hz, 1H); MS (ES$^+$) m/z: [M+1]$^+$ 497.11

Intermediate 24

2-[bis(methylsulfonyl)amino]-N-tert-butyl-5-({[tert-butyl(diphenyl)silyl]oxy}methyl)benzenesulfonamide

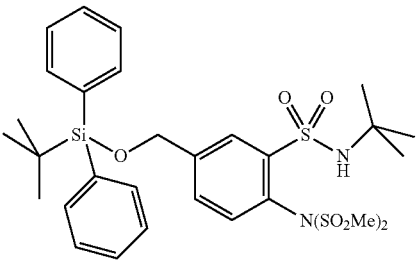

Methanesulfonyl chloride (27.6 g, 241 mmol) was added dropwise to a stirred mixture of 2-amino-N-tert-butyl-5-({[tert-butyl(diphenyl)silyl]oxy}methyl)benzenesulfonamide (57 g, 115 mmol) and triethylamine (24.4 g, 241 mmol) in DCM (200 mL) at 0° C. The reaction mixture was stirred at 0° C. for half an hour and then at room temperature for one hour. The reaction mixture was diluted with DCM (700 mL), washed with water (500 mL), saturated sodium bicarbonate (500 mL) and brine (500 mL). The organic layer was separated, dried over anhydrous sodium sulfate and concentrated under reduced pressure to yield the title compound (74.9 g, 100%). $^1$H NMR (400 MHz, CHLOROFORM-d) δ ppm 1.12 (s, 9H) 1.31 (s, 9H) 3.57 (s, 6H) 4.82 (s, 2H) 5.22 (s, 1H) 7.39 (m, 7H) 7.60 (d, 1H) 7.67 (d, 4H) 8.23 (d, J=2.00 Hz, 1H)

Intermediate 25

N-tert-butyl-5-({[tert-butyl(diphenyl)silyl]oxy}methyl)-2-[(methylsulfonyl)amino]benzenesulfonamide

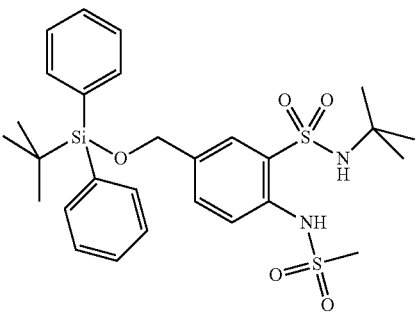 [SMILES: CC(C)(C)NS(=O)(=O)c1cc(CO[Si](c2ccccc2)(c2ccccc2)C(C)(C)C)ccc1NS(C)(=O)=O]

2M aqueous NaOH (173 mL, 345 mmol) was added to a stirred solution of 2-[bis(methylsulfonyl)amino]-N-tert-butyl-5-({[tert-butyl(diphenyl)silyl]oxy}methyl)benzenesulfonamide (74.92 g, 115 mmol) in THF (270 mL) at room temperature. The resulting mixture was stirred for 2 h, neutralized using 2M hydrochloric acid and extracted with DCM (2×500 mL). The combined extracts were washed

Intermediate 26

N-tert-butyl-2-({[2-(2-{[tert-butyl(dimethyl)silyl]oxy}-4-chlorophenyl)ethyl]sulfonyl}amino)-5-({[tert-butyl(diphenyl)silyl]oxy}methyl)benzenesulfonamide

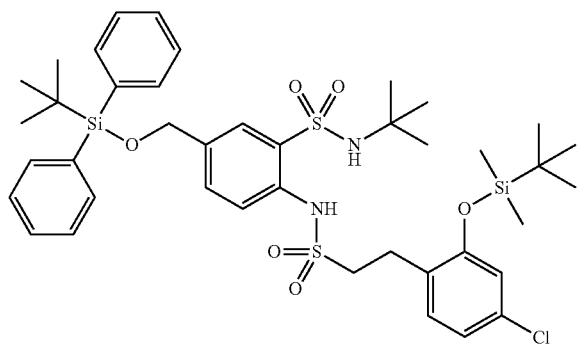 [SMILES: CC(C)(C)NS(=O)(=O)c1cc(CO[Si](c2ccccc2)(c2ccccc2)C(C)(C)C)ccc1NS(=O)(=O)CCc1ccc(Cl)cc1O[Si](C)(C)C(C)(C)C]

A solution of N-tert-butyl-5-({[tert-butyl(diphenyl)silyl]oxy}methyl)-2-[(methylsulfonyl)-amino]benzenesulfonamide (7.70 g, 13.40 mmol) was treated at −78° C. with lithium diisopropylamide (21.45 ml, 42.89 mmol). After 10 min a solution of [2-(bromomethyl)-5-chlorophenoxy](tert-butyl)dimethylsilane (4.5 g, 13.40 mmol) in THF (15 mL) was added dropwise under 50 min. The reaction mixture was stirred at −78° C. for 1.5 h then allowed to reach r.t., stirred for 1.5 h. The reaction mixture was quenched with brine extraction with ethyl acetate. The organic layer was washed with brine, dried over magnesium sulfate, filtered and concentrated under reduced pressure. Purification by chromatography on silica using gradient elution 12-20% EtOAc in heptane, yielded the title compound (6.55 g, 59%). $^1$H NMR (500 MHz, DMSO-$d_6$) δ ppm 0.17 (s, 6H) 0.87 (s, 9H) 1.00-1.05 (m, 9H) 1.07 (s, 9H) 2.93-3.05 (m, 2H) 3.40-3.52 (m, 2H) 4.79 (s, 2H), 6.78 (d, 1H) 6.96 (dd, 1H) 7.20 (d, 1H) 7.37-7.44 (m, 4H) 7.44-7.49 (m, 2H) 7.51 (dd, 1H) 7.60-7.68 (m, 5H) 7.98 (s, 1H) 8.01 (s, 1H) 8.73 (s, 1H) MS with water (500 mL) and brine (500 mL), dried over anhydrous sodium sulfate and concentrated under reduced pressure to yield the title compound (58 g, 88%). $^1$H NMR (400 MHz, CHLOROFORM-d) δ ppm 1.10 (s, 9H) 1.23 (s, 9H) 3.16 (s, 3H) 4.75 (s, 2H) 4.99 (s, 1H) 7.63 (m, 5H) 7.43 (m, 7H) 7.97 (d, J=2.00 Hz, 1H) 8.29 (s, 1H); MS (ES$^-$) m/z: 573.29[M−1]$^-$

Intermediate 27

N-tert-butyl-5-({[tert-butyl(diphenyl)silyl]oxy}methyl)-2-({[2-(4-chloro-2-hydroxyphenyl)ethyl]sulfonyl}amino)benzenesulfonamide

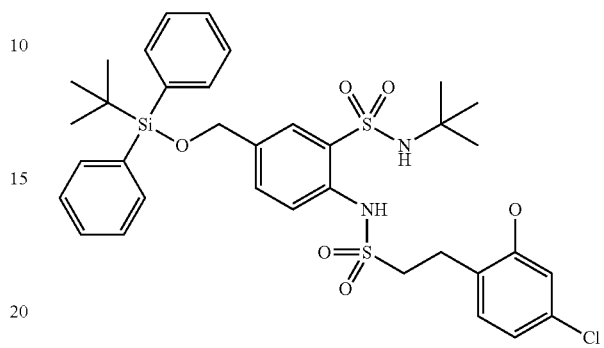

To a cold (0° C.) solution of N-tert-butyl-2-({[2-(2-{[tert-butyl(dimethyl)silyl]oxy}-4-chlorophenyl)-ethyl]sulfonyl}amino)-5-({[tert-butyl(diphenyl)silyl]oxy}methyl)benzenesulfonamide (6.55 g, 7.89 mmol) in THF (60 ml) was tetrabutylammonium fluoride (4.25 ml, 11.84 mmol) added. The reaction mixture was allowed to reach r.t., stirred for 1.5 h, more of tetrabutylammonium fluoride (4.14 ml, 11.84 mmol) was added, more tetrabutylammonium fluoride (4.14 ml, 11.84 mmol) was added after 30 min stirred for another 30 min. The reaction mixture was quenched by addition of sat. Brine, extracted with ethylacetate, the organic layer was washed with sat. aq. NH4Cl, dried over magnesium sulfate, filtered and concentrated under reduced pressure. Purification by chromatography on silica using gradient elution 25-50% EtOAc in heptane followed by EtOAc 100%, yielded the title compound (5.6 gr 99%). $^1$H NMR (500 MHz, DMSO-$d_6$) δ ppm 1.03 (s, 9H) 1.09 (s, 9H) 2.88-2.99 (m, 2H) 3.42-3.55 (m, 2H) 4.79 (s, 2H) 6.70-6.81 (m, 2H) 7.08 (d, 1H) 7.38-7.44 (m, 4H) 7.44-7.54 (m, 3H) 7.59-7.69 (m, 5H) 8.01 (d, 2H) 8.74 (s, 1H) 10.06 (s, 1H); MS (ES$^-$) m/z 713, 715, 717 [M-H]$^-$.

Intermediate 28

N-tert-butyl-5-({[tert-butyl(diphenyl)silyl]oxy}methyl)-2-[({2-[4-chloro-2-(2-phenylethoxy)phenyl]ethyl}sulfonyl)amino]benzenesulfonamide

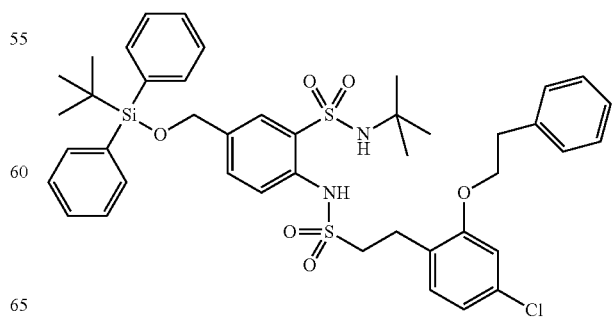

A mixture of N-tert-butyl-5-((tert-butyldiphenylsilyloxy) methyl)-2-(2-(4-chloro-2-hydroxyphenyl)ethylsulfonamido)benzenesulfonamide (1.2 g, 1.68 mmol), cesium carbonate (2.459 g, 7.55 mmol) and (2-bromoethyl)benzene (1.031 mL, 7.55 mmol) in N,N-dimethylformamide (10 mL) was heated in MW at 110° C. for 1 h 30 min. The solvent was evaporated and the crude product was taken up in water/ethyl acetate. The aqueous phase was extracted twice with ethyl acetate. The combined organic extracts were washed with ½ saturated brine, brine, dried over magnesium sulfate, filtered and the solvent was evaporated under reduced pressure. Purification by chromatography on silica using gradient elution 5-50% EtOAc in heptane, yielded the title compound (0.940 g, 68.4%). $^1$H NMR (500 MHz, DMSO-$d_6$) δ ppm 1.02 (s, 9H) 1.10 (s, 9H) 2.84 (t, 2H) 2.89-2.95 (m, 2H) 3.40-3.45 (m, 2H) 4.11 (t, 2H) 4.73 (s, 2H) 6.89 (dd, 1H) 7.00 (d, 1H) 7.12-7.19 (m, 2H) 7.23 (d, 4H) 7.38-7.43 (m, 4H) 7.44-7.52 (m, 3H) 7.59-7.65 (m, 5H) 8.01-8.05 (m, 2H) 8.76 (s, 1H); MS (ES$^-$) m/z 817, 819 [M-H]$^-$.

N-tert-butyl-2-[({2-[4-chloro-2-(2-phenylethoxy) phenyl]ethyl}sulfonyl)amino]-5-(hydroxymethyl) benzenesulfonamide

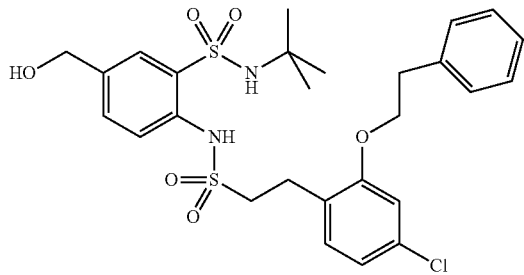 [SMILES: CC(C)(C)NS(=O)(=O)c1cc(CO)ccc1NS(=O)(=O)CCc1ccc(Cl)cc1OCCc1ccccc1]

Tetrabutylammonium fluoride (1M in THF) (4.59 mL, 4.59 mmol) was added to N-tert-butyl-5-({[tert-butyl(diphenyl)silyl]oxy}methyl)-2-[({2-[4-chloro-2-(2-phenylethoxy) phenyl]ethyl}-sulfonyl)amino]benzenesulfonamide (0.94 g, 1.15 mmol) in anhydrous tetrahydrofuran (20 mL). The mixture was stirred at room temperature over night. The solvent was evaporated and the crude product was dissolved in ethyl acetate. The organic phase was washed with water, brine, dried over magnesium sulfate, filtered and the solvent was under evaporated reduced pressure. Purification by chromatography on silica using gradient elution 5-100% EtOAc in heptane, yielded the title compound (0.565 g, 85%). $^1$H NMR (500 MHz, DMSO-$d_6$) δ ppm 1.10 (s, 9H) 2.86-2.94 (m, 4H) 3.38-3.43 (m, 2H) 4.12 (t, 2H) 4.48 (d, 2H) 5.39 (t, 1H) 6.89 (dd, 1H) 7.00 (d, 1H) 7.12 (d, 1H) 7.18-7.22 (m, 1H) 7.25-7.28 (m, 4H) 7.51 (dd, 1H) 7.62 (d, 1H) 7.87-7.88 (m, 1H) 7.99 (s, 1H) 8.75 (s, 1H); MS (ES−) m/z 579.58 [M-H]$^-$.

Example 10

2-(2-(4-chloro-2-phenethoxyphenyl)ethylsulfonamido)-5-(hydroxymethyl)-benzenesulfonamide

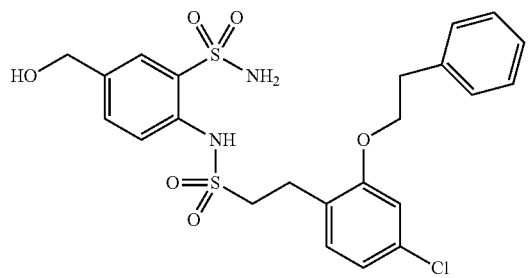 [SMILES: NS(=O)(=O)c1cc(CO)ccc1NS(=O)(=O)CCc1ccc(Cl)cc1OCCc1ccccc1]

N-tert-butyl-2-(2-(4-chloro-2-phenethoxyphenyl)ethylsulfonamido)-5-(hydroxymethyl)-benzenesulfonamide (372 mg, 0.64 mmol) was dissolved in trifluoroacetic acid (1.5 mL, 19.47 mmol) and stirred for 2.5 h. The reaction mixture was coevaporated with toluene. Purification by preparative HPLC gave the title compound (0.024 g, 7.2%). $^1$H NMR (500 MHz, DMSO-$d_6$) δ ppm 2.90 (t, 4H) 3.35-3.46 (m, 2H) 4.13 (t, 2H) 4.47 (d, 2H) 5.39 (br. s., 1H) 6.88 (dd, 1H) 7.00 (d, 1H) 7.12 (d, 1H) 7.17-7.23 (m, 1H) 7.28 (d, 5H) 7.51 (d, 1H) 7.60 (d, 1H) 7.82 (m, 2H) 7.86 (m 1H) 8.89 (m, 1H); MS (ES$^-$) m/z 523, 525, 527 [M-H]$^-$.

Biological Assays
Assays for Determining Biological Activity
Inhibition of Prostaglandin E Synthase Activity Compounds were tested as inhibitors of microsomal prostaglandin E synthase activity in microsomal prostaglandin E synthase assays and whole cell assays. These assays measure prostaglandin E2 (PGE2) synthesis, which is taken as a measure of prostaglandin E synthase activity. Microsomal prostaglandin E synthase biochemical assays used microsomal prostaglandin E synthase-1 in microsomal preparations. The source of the microsomes can be for example interleukin-1β-stimulated human A549 cells (which express human mPGES-1) or Sf9 cells transfected with plasmids encoding human mPGES-1 cDNA.

The whole blood assay [described by Patrignani, P. et al, Journal of Pharmacology and Experimental Therapeutics, 1994, vol. 271, pp 1705-1712] was used as the whole cell assay for testing the compounds. Whole blood provides a protein and cell rich environment for the study of biochemical efficacy of anti-inflammatory compounds, such as prostaglandin synthase inhibitors. To study the inhibitory activities of these compounds, human blood was stimulated with lipopolysaccharide (LPS) for typically 16 hours to induce mPGES-1 expression, after which the concentration of produced PGE2 was measured by competitive-immuno assay (homogeneous time-resolved fluorescence, HTRF) as read out for effectiveness against mPGES-1-dependent PGE2 production.

Microsomal Prostaglandin E Synthase Biochemical Assay

A solution of test compound was added to a diluted microsome preparation containing human mPGES-1 and pre-incubated for 15 minutes in potassium phosphate buffer pH 6.8 with cofactor glutathione (GSH). Corresponding solutions without test compound were used as positive controls, and corresponding solutions without test compound and without microsomes were used as negative controls. The enzymatic reaction was then started by addition of the substrate PGH2 in an organic solution (dry acetonitrile).

The typical reaction conditions of the enzymatic reaction were thus: Test compound: ranging from 60 μM to 0.002 μM, or zero in positive and negative controls; potassium phosphate buffer pH 6.8: 50 mM; GSH: 2.5 mM; mPGES-1-containing microsomes: 2 μg/mL (sample and positive controls) or 0 μg/mL (negative control); PGH2: 10.8 μM; Acetonitrile: 7.7% (v/v); DMSO: 0.6% (v/v). The reaction was stopped after one minute by adding an acidic solution (pH 1.9) of ferric chloride and citrate (final concentrations 7 mM and 47 mM respectively), by which the PGH2 was sequestered (the PGH2 is reduced to mainly 12-hydroxy heptadecatrineoic acid (12-HHT) which is not detected by the subsequent PGE2 detection step). The resulting solution was then pH neutralized by addition of potassium phosphate buffer, prior to diluting an aliquot of the resulting solution in a weak potassium phosphate buffer (50 mM, pH 6.8) containing 0.2% BSA (w/v). [Adapted from Jacobsson et al., Proc. Natl. Acad. Sci. USA, 1999, vol. 96, pp. 7220-7225] The PGE2 formed was quantified by use of a commercial HTRF based kit (catalogue #62PG2PEC or #62P2APEC from Cisbio International). 100% activity was defined as the PGE2 production in positive controls subtracted by the PGE2 production in the negative controls. IC50 values were then determined using standard procedures.

Data from this assay for representative compounds is shown in the Table below. The potency is expressed as IC50 and the value indicated is an average of at least n=2. The data indicate that the compounds of the invention are expected to possess useful therapeutic properties.

Results

| Example | mPGES (nM) | hWBA (nM) |
|---|---|---|
| 1 | 6.96 | 50.8 |
| 2 | 3.7 | 3.4 |
| 3 | 6.4 | 90.0 |
| 4 | 26.4 | 70.3 |
| 5 | 4.1 | 10.4 |
| 6 | 13.6 | 77.4 |
| 7 | 19.9 | 76.5 |
| 8 | 7.3 | 33.6 |
| 9 | 11.9 | 84.3 |
| 10 | 7.97 | 10.6 |

Whole Blood Assay

Human blood collected from human volunteers in heparinized tubes was incubated with 100 μM acetyl salicylic acid, in order to inhibit the constitutively expressed cyclooxygenase (COX)-1/COX-2 enzymes, and then stimulated with 0.1 μg/ml LPS to induce the expression of enzymes along the COX-2 pathway, e.g. COX-2 and mPGES-1. 100 μL of this blood was added to the wells of a 384-well plate containing 1 μL DMSO solutions of compounds typically in the final concentration range 316 μM to 0.01 μM. Naproxen was used as reference compound. The mix was incubated at 37° C. for 16 hours. Plasma was harvested by centrifugation and stored at −70° C. until further analysis of PGE2 levels. For the calculations, the 0%-activity value was represented by blood treated with acetyl salicylic acid, LPS and the reference compound (1 mM Naproxen). The 100%-activity value was represented by blood treated with aspirin, LPS and DMSO. [Reference: Patrignani, P. et al, Journal of Pharmacology and Experimental Therapeutics, 1994, vol. 271, pp 1705-1712]. The PGE2 formed was quantified, after dilution in a weak potassium phosphate buffer (50 mM, pH 6.8) containing 0.2% BSA (w/v), by use of a commercial HTRF based kit (catalogue #62PG2PEC or #62P2APEC from Cisbio International). IC50 values were then determined using standard procedures.

The results show that the novel bis(sulfonamide) compounds are selective inhibitors of the microsomal prostaglandin E synthase-1 enzyme. The compounds have an improved potency and selectivity.

The invention claimed is:

1. A compound of formula (I), or a pharmaceutically acceptable salt thereof

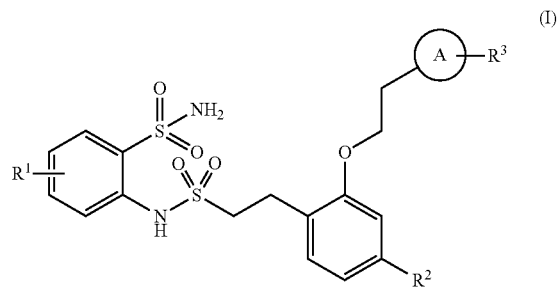

wherein:

A is phenyl or a saturated or unsaturated 9 or 10 membered-ring optionally comprising one or two heteroatoms selected from 0 and N;

$R^1$ is H, halogen or —$CH_2OH$;

$R^2$ is H, halogen, $C_{1-4}$-alkyl, fluoro-$C_{1-4}$-alkyl or —C≡C—$R^4$;

$R^3$ is H, halogen, $C_{1-4}$-alkyl, $C_{1-4}$-alkoxy, cyano or oxo; and $R^4$ is $C_{1-4}$-alkyl, $C_{3-7}$-cycloalkyl or phenyl, wherein phenyl is optionally substituted with one or more substituents independently selected from $C_{1-4}$-alkyl, halogen, $C_{1-4}$-alkoxy and cyano.

2. The compound of formula (I) according to claim 1, wherein

A is phenyl, indolyl or dihydroindolyl;

$R^1$ is H or —$CH_2OH$;

$R^2$ is H, bromine, chlorine, fluorine, $C_{1-4}$-alkyl, fluoro-$C_{1-4}$-alkyl or —C≡C—$R^4$;

$R^3$ is H, bromine, chlorine, fluorine, $C_{1-4}$-alkyl, $C_{1-4}$-alkoxy, cyano or oxo; and $R^4$ is $C_{1-4}$-alkyl, $C_{3-7}$-cycloalkyl or phenyl, wherein phenyl is optionally substituted with $C_{1-4}$-alkyl.

3. The compound of formula (I) according to claim 1, wherein

A is phenyl, indolyl or dihydroindolyl;

$R^1$ is H;

$R^2$ is chlorine; and $R^3$ is H, $C_{1-2}$-alkyl, $C_{1-2}$-alkoxy, cyano or oxo.

4. The compound of formula (I) according to claim 1, wherein

A is phenyl;

$R^1$ is H or —$CH_2OH$;

$R^2$ is H, chlorine, $C_{1-4}$-alkyl or fluoro-$C_{1-4}$-alkyl; and $R^3$ is H, $C_{1-2}$-alkyl, $C_{1-2}$-alkoxy, cyano or oxo.

5. The compound of formula (I) according to claim 1, wherein A is phenyl and $R^1$ is H.

6. The compound of formula (I) according to claim 1, wherein A is indolyl or dihydroindolyl and $R^1$ is H.

7. The compound of formula (I) according to claim 1, wherein R² is chlorine.

8. A compound, or a pharmaceutically acceptable salt thereof, selected from the group consisting of
- 2-(2-(4-chloro-2-phenethoxyphenyl)ethylsulfonamido)benzenesulfonamide,
- 2-(2-(4-chloro-2-(2-methoxyphenethoxy)phenyl)ethylsulfonamido)benzenesulfonamide,
- 2-(2-(4-chloro-2-(3-methoxyphenethoxy)phenyl)ethylsulfonamido)benzenesulfonamide,
- 2-(2-(4-chloro-2-(4-methoxyphenethoxy)phenyl)ethylsulfonamido)benzenesulfonamide,
- 2-(2-(4-chloro-2-(2-cyanophenethoxy)phenyl)ethylsulfonamido)benzenesulfonamide,
- 2-(2-(4-chloro-2-(3-cyanophenethoxy)phenyl)ethylsulfonamido)benzenesulfonamide,
- 2-(2-(4-chloro-2-(4-cyanophenethoxy)phenyl)ethylsulfonamido)benzenesulfonamide,
- 2-(2-(4-chloro-2-(2-(1-methyl-1H-indol-4-yl)ethoxy)phenyl)ethylsulfonamido)benzenesulfonamide,
- 2-(2-(4-chloro-2-(2-(2-oxoindolin-4-yl)ethoxy)phenyl)ethylsulfonamido)benzenesulfonamide, and
- 2-(2-(4-chloro-2-phenethoxyphenyl)ethylsulfonamido)-5-(hydroxymethyl)benzenesulfonamide.

9. A method of treating pain in a patient comprising administering to the patient a compound of formula (I), or a pharmaceutically acceptable salt thereof, according to claim 1.

10. The method of claim 9, wherein the pain is acute or chronic pain, nociceptive pain or neuropathic pain.

11. A method of treating cancer in a patient comprising administering to the patient a compound of formula (I), or a pharmaceutically acceptable salt thereof, according to claim 1, wherein the cancer is bone cancer, colorectal cancer, or non-small-cell lung cancer.

12. A method of treating apnea, atherosclerosis, aneurysm, hyperthermia, myositis, Alzheimer's disease or arthritis in a patient comprising administering to the patient a compound of formula (I), or a pharmaceutically acceptable salt thereof, according to claim 1.

13. A method of modulating microsomal prostaglandin E synthase-1 activity comprising administering to a patient an effective amount of a compound of formula (I) or a pharmaceutically acceptable salt thereof according to claim 1.

14. A pharmaceutical composition comprising the compound of formula (I), or a pharmaceutically acceptable salt thereof, according to claim 1 in association with a pharmaceutically acceptable adjuvant, diluent, or carrier.

15. A process for the preparation of a pharmaceutical composition according to claim 14 comprising mixing a compound of formula (I) or a pharmaceutically acceptable salt thereof

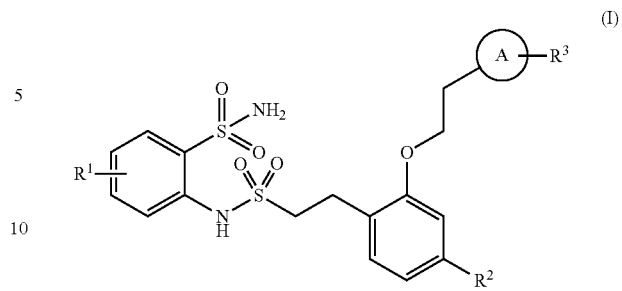

wherein:
- A is phenyl or a saturated or unsaturated 9 or 10 membered-ring optionally comprising one or two heteroatoms selected from O and N;
- $R^1$ is H, halogen or —CH₂OH;
- $R^2$ is H, halogen, $C_{1-4}$-alkyl, fluoro-$C_{1-4}$-alkyl or —C≡C—$R^4$;
- $R^3$ is H, halogen, $C_{1-4}$-alkyl, $C_{1-4}$-alkoxy, cyano or oxo; and
- $R^4$ is $C_{1-4}$-alkyl, $C_{3-7}$-cycloalkyl or phenyl, wherein phenyl is optionally substituted with one or more substituents independently selected from $C_{1-4}$-alkyl, halogen, $C_{1-4}$-alkoxy and cyano;

with a pharmaceutically acceptable adjuvant, diluent or carrier.

16. A method of modulating microsomal prostaglandin E synthase-1 activity comprising administering to a patient a pharmaceutical composition according to claim 14.

17. The pharmaceutical composition according to claim 14, further comprising an additional therapeutic agent.

18. The pharmaceutical composition according to claim 17, wherein the additional therapeutic agent is selected from the group consisting of acetyl cholinesterase inhibitors, anti-inflammatory agents, cognitive enhancing agents, memory enhancing agents and atypical antipsychotic agents.

19. The method of claim 12, for treating apnea in the patient.

20. The method of claim 12, for treating atherosclerosis in the patient.

21. The method of claim 12, for treating aneurysm in the patient.

22. The method of claim 12, for treating hyperthermia in the patient.

23. The method of claim 12, for treating myositis in the patient.

24. The method of claim 12, for treating Alzheimer's disease in the patient.

25. The method of claim 12, for treating arthritis in the patient.

* * * * *